(12) United States Patent
Yang et al.

(10) Patent No.: US 12,030,951 B2
(45) Date of Patent: Jul. 9, 2024

(54) ANTI-OX40 ANTIBODY AND USES THEREOF

(71) Applicant: HUTCHISON MEDIPHARMA LIMITED, Shanghai (CN)

(72) Inventors: Yizhen Yang, Shanghai (CN); Yu Cai, Shanghai (CN); Xiong Li, Shanghai (CN); Lei Zhou, Shanghai (CN); Weiguo Qing, Shanghai (CN); Wei-Guo Su, Shanghai (CN)

(73) Assignee: HUTCHISON MEDIPHARMA LIMITED, Shanghai (CN)

( * ) Notice: Subject to any disclaimer, the term of this patent is extended or adjusted under 35 U.S.C. 154(b) by 0 days.

(21) Appl. No.: 17/820,682

(22) Filed: Aug. 18, 2022

(65) Prior Publication Data

US 2023/0151105 A1    May 18, 2023

Related U.S. Application Data

(63) Continuation of application No. PCT/CN2021/087616, filed on Apr. 16, 2021.

(30) Foreign Application Priority Data

Apr. 17, 2020 (CN) .......................... 202010304381.8

(51) Int. Cl.
*C07K 16/28* (2006.01)
*A61K 47/68* (2017.01)
(Continued)

(52) U.S. Cl.
CPC ...... *C07K 16/2878* (2013.01); *A61K 47/6849* (2017.08); *A61P 17/00* (2018.01); *A61P 35/04* (2018.01); *A61P 37/02* (2018.01); *A61P 37/06* (2018.01); *C12N 15/63* (2013.01); *A61K* *2039/505* (2013.01); *C07K 2317/24* (2013.01); *C07K 2317/565* (2013.01); *C07K 2317/71* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 5,225,539 A | 7/1993 | Winter |
| 5,530,101 A | 6/1996 | Queen et al. |

(Continued)

FOREIGN PATENT DOCUMENTS

| CN | 110092832 A | 8/2019 |
| WO | WO 00/42072 A2 | 7/2000 |

(Continued)

OTHER PUBLICATIONS

Sela-Culang et al., The structural basis of antibody-antigen recognition, Front. Immunol. 4:302, 13 pages, Oct. 2013.*

(Continued)

*Primary Examiner* — Claire Kaufman
(74) *Attorney, Agent, or Firm* — Hoxie & Associates LLC

(57) ABSTRACT

The present invention provides an anti-OX40 antibody or antigen-binding fragment thereof, a preparation method therefor and the use for treating OX40-related diseases or conditions.

13 Claims, 3 Drawing Sheets

Specification includes a Sequence Listing.

Antibody Hu38E11 blocks binding of OX40 to OX40L

(51) Int. Cl.
*A61P 17/00* (2006.01)
*A61P 35/04* (2006.01)
*A61P 37/02* (2006.01)
*A61P 37/06* (2006.01)
*C12N 15/63* (2006.01)
*A61K 39/00* (2006.01)

(56) References Cited

U.S. PATENT DOCUMENTS

| | | |
|---|---|---|
| 5,585,089 A | 12/1996 | Queen et al. |
| 5,693,762 A | 12/1997 | Queen et al. |
| 6,171,586 B1 | 1/2001 | Lam et al. |
| 6,180,370 B1 | 1/2001 | Queen et al. |
| 6,267,958 B1 | 7/2001 | Andya et al. |
| 10,259,882 B2 * | 4/2019 | Van Dijk ........... C07K 16/2875 |
| 2018/0057598 A1 | 3/2018 | Lazar et al. |
| 2021/0024640 A1 | 1/2021 | Calzone et al. |
| 2021/0214452 A1 | 7/2021 | Liu et al. |

FOREIGN PATENT DOCUMENTS

| | | |
|---|---|---|
| WO | WO 2004/092219 A2 | 10/2004 |
| WO | WO 2006/044908 A2 | 4/2006 |
| WO | WO 2009/079335 A1 | 6/2009 |
| WO | WO 2013/008171 A1 | 1/2013 |
| WO | WO 2014/089113 A1 | 6/2014 |
| WO | WO 2015/153513 A1 | 10/2015 |
| WO | WO 2016/057667 | 4/2016 |
| WO | WO 2019/089921 A1 | 5/2019 |
| WO | WO 2019/100320 A1 | 5/2019 |
| WO | WO 2019/144677 A1 | 8/2019 |
| WO | WO 2019/178852 A1 | 9/2019 |

OTHER PUBLICATIONS

Carvalho et al., Regulatory and Scientific Advancements in Gene Therapy: State-of-the-Art of Clinical Applications and of the supporting European Regulatory Framework, Front. Med. 4:182, doi: 10.3389/fmed.2017.00182, 18 pages, Oct. 2017.*
Bruhns et al., "Mouse and Human FcR Effector Functions," Immunological Reviews, vol. 268, p. 25-51, (2015).
Capel et al., "Heterogeneity of Human IgG Fc Receptors," Immunomethods, vol. 4, p. 25-34, (1994).
Chothia et al., "Canonical Structures for the Hypervariable Regions of Immunoglobulins," J Mol Biol. vol. 196, p. 901-917, (1987).
Daëron, M., "Fc Receptor Biology," Annu Rev Immunol., vol. 15, p. 203-234, (1997).
Flatman et al., "Process Analytics for Purification of Monoclonal Antibodies," Journal of Chromatography B, vol. 848, p. 79-87, (2007).
Ghetie et al., "FcRn: The MHC Class I-related Receptor That is More Than an IgG Transporter," Immunology Today, vol. 18, No. 12, p. 592-598, (1997).
Ghetie et al., "Increasing the Serum Persistence of an IgG Fragment by Random Mutagenesis," Nature Biotechnology, vol. 15, p. 637-640, (1997).
Guyer et al., "Immunoglobulin Binding by Mouse Intestinal Epithelial Cell Receptors," vol. 117, No. 2, p. 587-593, (1976); Abstract only.
Hinton et al., "Engineered Human IgG Antibodies with Longer Serum Half-lives in Primates," The Journal of Biological Chemistry, vol. 279, No. 8, p. 6213-6216, (2004).
Kim et al., "Localization of the Site of the Murine IgG1 Molecule That is Involved in Binding to the Murine Intestinal Fc Receptor," Eur J Immunol., vol. 24, p. 2429-2434, (1994).
Liu et al., "Chimeric Mouse-human IgG1 Antibody That Can Mediate Lysis of Cancer Cells," Proc Natl Acad Sci., vol. 84, p. 3439-3443, (1987).
North et al., "A New Clustering of Antibody CDR Loop Conformations," J Mol Biol., vol. 406, No. 2, p. 228-256, (2011).
Ravetch et al., "Fc Receptors," Annu Rev Immunol., vol. 9, p. 457-492, (1991).
Shields et al., "High Resolution Mapping of the Binding Site on Human IgG1 for FcγRI, FcγRII, FcγRIII, and FcRn and Design of IgG1 Variants with Improved Binding to the FcγR," The Journal of Biological Chemistry, vol. 276, No. 9, p. 6591-6604, (2001).
Vidarsson et al., "IgG Subclasses and Allotypes: From Structure to Effector Functions," Frontiers in Immunology, vol. 5, No. 520, p. 1-17, (2014).
Wang et al., "IgG Fc Engineering to Modulate Antibody Effector Functions," Protein Cell, vol. 9, No. 1, p. 63-73, (2018).
Wang et al., "An Integrative Approach to Inform Optimal Administration of OX40 Agonist Antibodies in Patients with Advanced Solid Tumors", *Clinical Cancer Research*, 25(22); pp. 6709-6720, (2019).
Griffiths et al., "Domain Binding and Isotype Dictate the Activity of Anti-human OX40 Antibodies," Journal for ImmunoTherapy of Cancer, vol. 8, No. e001557, 14 pages, (2020).

* cited by examiner

SEQUENCE LISTING

```
Sequence total quantity: 22
SEQ ID NO: 1          moltype = AA  length = 120
FEATURE               Location/Qualifiers
REGION                1..120
                      note = synthetic
source                1..120
                      mol_type = protein
                      organism = synthetic construct
SEQUENCE: 1
QVQLQQPGAE LVRPGSSVQL SCKASGYTFT SYWVDWVKQR PGQGLQWIGN IYPSDSETHY  60
NQKFKDKATL TVDKSSSTAY MQLSSLTSED SAVYYCARSY GYYGTWFAYW GQGTLVTVSA 120

SEQ ID NO: 2          moltype = AA  length = 120
FEATURE               Location/Qualifiers
REGION                1..120
                      note = synthetic
source                1..120
                      mol_type = protein
                      organism = synthetic construct
SEQUENCE: 2
QVQLVQSGAE VKKPGASVKV SCKASGYTFT SYWVDWVRQA PGQGLEWMGN IYPSDSETHY  60
NQKFKDRVTM TRDTSTSTVY MELSSLRSED TAVYYCARSY GYYGTWFAYW GQGTLVTVSS 120

SEQ ID NO: 3          moltype = AA  length = 120
```

```
FEATURE                 Location/Qualifiers
REGION                  1..120
                        note = synthetic
source                  1..120
                        mol_type = protein
                        organism = synthetic construct
SEQUENCE: 3
QVQLVQSGAE VKKPGASVKV SCKASGYTFT SYWVDWVRQA PGQGLEWIGN IYPSDSETHY    60
NQKFKDRVTM TVDTSTSTVY MELSSLRSED TAVYYCARSY GYYGTWFAYW GQGTLVTVSS   120

SEQ ID NO: 4            moltype = AA   length = 120
FEATURE                 Location/Qualifiers
REGION                  1..120
                        note = synthetic
source                  1..120
                        mol_type = protein
                        organism = synthetic construct
SEQUENCE: 4
QVQLVQSGAE VKKPGASVKV SCKASGYTFT SYWVDWVRQA PGQGLEWIGN IYPSDSETHY    60
NQKFKDRVTM TVDTSTSTAY MELSSLRSED SAVYYCARSY GYYGTWFAYW GQGTLVTVSS   120

SEQ ID NO: 5            moltype = AA   length = 120
FEATURE                 Location/Qualifiers
REGION                  1..120
                        note = synthetic
source                  1..120
                        mol_type = protein
                        organism = synthetic construct
SEQUENCE: 5
QVQLVQSGAE VKKPGASVKL SCKASGYTFT SYWVDWVRQA PGQGLEWIGN IYPSDSETHY    60
NQKFKDKVTL TVDTSTSTAY MELSSLRSED SAVYYCARSY GYYGTWFAYW GQGTLVTVSS   120

SEQ ID NO: 6            moltype = AA   length = 111
FEATURE                 Location/Qualifiers
REGION                  1..111
                        note = synthetic
source                  1..111
                        mol_type = protein
                        organism = synthetic construct
SEQUENCE: 6
DIVLTQSPAS LAVSLGQRAT ISCRASESVD SSGNSFMHWY QQKPGQPPKL LIYRASNLES    60
GIPARFSGSG SRTDFTLTIN PVEADDVATY YCQQSNEDPW TFGGGTKLEI K            111

SEQ ID NO: 7            moltype = AA   length = 111
FEATURE                 Location/Qualifiers
REGION                  1..111
                        note = synthetic
source                  1..111
                        mol_type = protein
                        organism = synthetic construct
SEQUENCE: 7
DIVMTQSPDS LAVSLGERAT INCRASESVD SSGNSFMHWY QQKPGQPPKL LIYRASNLES    60
GVPDRFSGSG SGTDFTLTIS SLQAEDVAVY YCQQSNEDPW TFGGGTKLEI K            111

SEQ ID NO: 8            moltype = AA   length = 111
FEATURE                 Location/Qualifiers
REGION                  1..111
                        note = synthetic
source                  1..111
                        mol_type = protein
                        organism = synthetic construct
SEQUENCE: 8
DIVMTQSPDS LAVSLGERAT INCRASESVD SSGNSFMHWY QQKPGQPPKL LIYRASNLES    60
GIPDRFSGSG SGTDFTLTIS SLQAEDVAVY YCQQSNEDPW TFGGGTKLEI K            111

SEQ ID NO: 9            moltype = AA   length = 111
FEATURE                 Location/Qualifiers
REGION                  1..111
                        note = synthetic
source                  1..111
                        mol_type = protein
                        organism = synthetic construct
SEQUENCE: 9
DIVMTQSPDS LAVSLGERAT INCRASESVD SSGNSFMHWY QQKPGQPPKL LIYRASNLES    60
GIPDRFSGSG SGTDFTLTIS SVQAEDVAVY YCQQSNEDPW TFGGGTKLEI K            111

SEQ ID NO: 10           moltype = AA   length = 111
FEATURE                 Location/Qualifiers
REGION                  1..111
```

-continued

```
                         note = synthetic
source                   1..111
                         mol_type = protein
                         organism = synthetic construct
SEQUENCE: 10
DIVLTQSPDS LAVSLGERAT INCRASESVD SSGNSFMHWY QQKPGQPPKL LIYRASNLES      60
GIPDRFSGSG SGTDFTLTIS SVQAEDVAVY YCQQSNEDPW TFGGGTKLEI K              111

SEQ ID NO: 11            moltype = AA   length = 5
FEATURE                  Location/Qualifiers
REGION                   1..5
                         note = synthetic
source                   1..5
                         mol_type = protein
                         organism = synthetic construct
SEQUENCE: 11
SYWVD                                                                   5

SEQ ID NO: 12            moltype = AA   length = 17
FEATURE                  Location/Qualifiers
REGION                   1..17
                         note = synthetic
source                   1..17
                         mol_type = protein
                         organism = synthetic construct
SEQUENCE: 12
NIYPSDSETH YNQKFKD                                                     17

SEQ ID NO: 13            moltype = AA   length = 11
FEATURE                  Location/Qualifiers
REGION                   1..11
                         note = synthetic
source                   1..11
                         mol_type = protein
                         organism = synthetic construct
SEQUENCE: 13
SYGYYGTWFA Y                                                           11

SEQ ID NO: 14            moltype = AA   length = 15
FEATURE                  Location/Qualifiers
REGION                   1..15
                         note = synthetic
source                   1..15
                         mol_type = protein
                         organism = synthetic construct
SEQUENCE: 14
RASESVDSSG NSFMH                                                       15

SEQ ID NO: 15            moltype = AA   length = 7
FEATURE                  Location/Qualifiers
REGION                   1..7
                         note = synthetic
source                   1..7
                         mol_type = protein
                         organism = synthetic construct
SEQUENCE: 15
RASNLES                                                                 7

SEQ ID NO: 16            moltype = AA   length = 9
FEATURE                  Location/Qualifiers
REGION                   1..9
                         note = synthetic
source                   1..9
                         mol_type = protein
                         organism = synthetic construct
SEQUENCE: 16
QQSNEDPWT                                                               9

SEQ ID NO: 17            moltype = AA   length = 360
FEATURE                  Location/Qualifiers
REGION                   1..360
                         note = synthetic
source                   1..360
                         mol_type = protein
                         organism = synthetic construct
SEQUENCE: 17
CAGGTCCAAC TGCAGCAGCC TGGGGCTGAG CTGGTGAGGC CTGGGTCTTC AGTGCAGTTG       60
TCCTGCAAGG CTTCTGGCTA CACCTTCACC AGCTACTGGG TGGATTGGGT GAAGCAGAGG      120
CCTGGACAAG GCCTTCAATG GATTGGTAAC ATTTACCCTT CTGATAGTGA AACTCACTAC      180
```

```
AATCAAAAGT TCAAGGACAA GGCCACATTG ACTGTAGACA AATCCTCCAG CACAGCCTAC    240
ATGCAGCTCA GCAGCCTGAC ATCTGAAGAC TCTGCGGTCT ATTACTGTGC AAGATCTTAT    300
GGTTACTACG GGACCTGGTT TGCTTACTGG GGCCAAGGGA CTCTGGTCAC TGTCTCTGCA    360

SEQ ID NO: 18           moltype = AA   length = 360
FEATURE                 Location/Qualifiers
REGION                  1..360
                        note = synthetic
source                  1..360
                        mol_type = protein
                        organism = synthetic construct
SEQUENCE: 18
CAGGTTCAGT TGGTTCAGTC TGGCGCCGAA GTGAAGAAAC CTGGCGCCTC TGTGAAGGTG     60
TCCTGCAAGG CTTCCGGCTA CACCTTTACC AGCTACTGGG TCGACTGGGT CCGACAGGCT    120
CCTGGACAAG GACTGGAATG GATGGGCAAC ATCTACCCCT CCGACTCCGA GACACACTAC    180
AACCAGAAAT TCAAGGACCG CGTGACCATG ACCAGAGACA CCTCCACCAG CACCGTGTAC    240
ATGGAACTGT CCAGCCTGAG ATCCGAGGAC ACCGCCGTGT ACTACTGCGC CAGATCCTAC    300
GGCTACTACG GCACTTGGTT TGCCTATTGG GGCCAGGGCA CACTGGTCAC CGTTTCTTCC    360

SEQ ID NO: 19           moltype = AA   length = 333
FEATURE                 Location/Qualifiers
REGION                  1..333
                        note = synthetic
source                  1..333
                        mol_type = protein
                        organism = synthetic construct
SEQUENCE: 19
GACATTGTGC TGACCCAATC TCCAGCTTCT TTGGCTGTGT CTCTAGGGCA GAGGGCCACC     60
ATATCCTGCA GAGCCAGTGA AAGTGTTGAT AGTTCTGGCA ATAGTTTTAT GCACTGGTAC    120
CAGCAGAAAC CAGGACAGCC ACCCAAACTC CTCATCTATC GGCATCAA CCTAGAATCT    180
GGGATCCCTG CCAGGTTCAG TGGCAGTGGG TCTAGGACAG ACTTCACCCT CACCATTAAT    240
CCTGTGGAGG CTGATGATGT TGCAACCTAT TACTGTCAGC AAAGTAATGA GGATCCGTGG    300
ACGTTCGGTG GAGGCACCAA ACTGGAAATC AAA                                 333

SEQ ID NO: 20           moltype = AA   length = 333
FEATURE                 Location/Qualifiers
REGION                  1..333
                        note = synthetic
source                  1..333
                        mol_type = protein
                        organism = synthetic construct
SEQUENCE: 20
GATATCGTGA TGACCCAGTC TCCTGACAGC CTGGCTGTGT CTCTGGGCGA GAGAGCCACC     60
ATCAACTGCA GAGCCTCTGA GTCCGTGGAC TCCTCCGGCA ACTCTTTCAT GCACTGGTAT    120
CAGCAGAAGC CCGGCCAGCC TCCTAAGCTG CTGATCTACA GAGCCTCCAA CCTGGAATCT    180
GGCGTGCCCG ACAGATTCTC CGGCTCTGGC TCTGGCACAG ACTTTACCCT GACCATCAGC    240
TCCCTGCAGG CCGAGGATGT GGCCGTGTAC TACTGCCAGC AGTCCAACGA GGACCCCTGG    300
ACATTTGGCG GCGGAACAAA GCTGGAAATC AAG                                 333

SEQ ID NO: 21           moltype = AA   length = 330
FEATURE                 Location/Qualifiers
REGION                  1..330
                        note = synthetic
source                  1..330
                        mol_type = protein
                        organism = synthetic construct
SEQUENCE: 21
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKRVEP KSCDKTHTCP PCPAPELLGG    120
PSVFLFPPKP KDTLMISRTP EVTCVVVDVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSREE    240
MTKNQVSLTC LVKGFYPSDI AVEWESNGQP ENNYKTTPPV LDSDGSFFLY SKLTVDKSRW    300
QQGNVFSCSV MHEALHNHYT QKSLSLSPGK                                     330

SEQ ID NO: 22           moltype = AA   length = 326
FEATURE                 Location/Qualifiers
REGION                  1..326
                        note = synthetic
source                  1..326
                        mol_type = protein
                        organism = synthetic construct
SEQUENCE: 22
ASTKGPSVFP LAPCSRSTSE STAALGCLVK DYFPEPVTVS WNSGALTSGV HTFPAVLQSS     60
GLYSLSSVVT VPSSNFGTQT YTCNVDHKPS NTKVDKTVER KCCVECPPCP APPVAGPSVF    120
LFPPKPKDTL MISRTPEVTC VVVDVSHEDP EVQFNWYVDG VEVHNAKTKP REEQFNSTFR    180
VVSVLTVVHQ DWLNGKEYKC KVSNKGLPAP IEKTISKTKG QPREPQVYTL PPSREEMTKN    240
QVSLTCLVKG FYPSDIAVEW ESNGQPENNY KTTPPMLDSD GSFFLYSKLT VDKSRWQQGN    300
VFSCSVMHEA LHNHYTQKSL SLSPGK                                         326
```

ANTI-OX40 ANTIBODY AND USES THEREOF

CROSS-REFERENCE TO RELATED APPLICATIONS

This application is a continuation of International Application No. PCT/CN2021/087616, filed on Apr. 16, 2021, which is based on and claims priority to CN 202010304381.8, which is filed on Apr. 17, 2020 and is entirely incorporated herein by reference for all purposes.

REFERENCE TO A SEQUENCE LISTING

This application contains a Sequence Listing as a separate part of the disclosure. The contents of the Sequence Listing (2022-08-018_HML-09-PCTC_Sequence_Listing_ST25.txt; Size: 31,256 bytes; and Date of Creation: Jul. 28, 2022) are incorporated herein by reference.

TECHNICAL FIELD

The present invention relates to an antibody, and in particular to an anti-OX40 antibody and antigen-binding fragment thereof, and method for preparing the antibody and use same for treating or preventing OX40-related diseases or conditions.

BACKGROUND ART

OX40 (also referred to as CD134, TNFRSF4 and ACT35) is a member of tumor-necrosis factor superfamily, which is mainly expressed on the surface of activated $CD4^+$ T cells, $CD8^+$ T cells and regulatory T cells, and also on the surface of natural killer cells (NK cells). In activated T cells, the costimulatory signal mediated by OX40L-OX40 can stimulate helper T cells to produce and secrete cytokines, stimulate effector T cells to release granzyme and perforin, and cause effector T cells and memory T cells to proliferate. At the same time, the OX40L-OX40 signal can also inhibit the differentiation and activity of regulatory T cells and reduce the immunosuppressive function of regulatory T cells, thereby further enhancing immunoreactions. The important role of OX40 in a T-cell immune response makes OX40 agonists an important candidate for tumor immunotherapy, while OX40 inhibitors have potential application values in inflammation, allergic diseases and autoimmune diseases.

In recent years, with a wide application of preparation techniques for monoclonal antibodies, monoclonal antibodies that specifically bind to OX40 have emerged, including two categories, i.e., OX40 agonists and OX40 inhibitors. Under physiological conditions, OX40 activates the corresponding signaling pathways in cells by binding to its ligand OX40L and trimerization. Therefore, OX40 agonist monoclonal antibodies always require cross-linking to function as an agonist antibody. Under in vitro and in vivo conditions, antibody cross-linking can be achieved by either coating on a solid surface or by Fc receptors, respectively. Fc receptors are a family of protein receptors that specifically bind to the Fc fragment of an antibody. In particular, Fcγ receptors can specifically bind to IgG and exert functions such as ADCC and ADCP. Fcγ receptors mainly include FcγRI, FcγRIIA, FcγRIIB, FcγRIIIA, FcγRIIIB, etc., which are expressed on the surface of a variety of blood cells, including B lymphocytes, dendritic cells, natural killer cells, macrophages, neutrophils, eosinophilic granulocytes, basophilic granulocytes, mast cells, platelets, etc. Under physiological conditions, Fcγ receptors can simultaneously bind to the Fc fragments of one or more IgG molecules, and achieve cross-linking of the IgG molecules while activating the receptor-mediated functions. OX40 agonist antibodies can activate OX40 molecules by binding to Fcγ receptors and cross-linking. OX40 antagonist antibodies can block the binding of OX40L to OX40, prevent the trimerization of OX40, thereby inhibiting OX40 activation-induced T cell activation and related inflammatory responses.

Tumor cells can escape the recognition and attack of an immune system through multiple mechanisms to achieve immune escape, survive in the body and proliferate excessively. An important mechanism that mediates tumor immune escape is by costimulatory molecules named as immune checkpoints that are highly expressed in immune cells or tumor cells in tumor microenvironment. Immune checkpoints can be divided, based on their functions, into inhibitory immune checkpoints, represented by PD-1, PD-L1, CTLA-4, etc.; and activating immune checkpoints, represented by OX40 and 4-1BB. For inhibitory immune checkpoints, drugs such as antibodies can be used to block their inhibitory function, which is like releasing the brakes on immune cells, allowing immune cells to play their role in killing tumor cells. Tumor immunotherapy represented by PD-1, PD-L1 and CTLA-4 is becoming a very important treatment means and exhibits exciting results in clinical applications. The use of agonists to activate agonistic immune checkpoints, analogous to stepping on the gas pedal after releasing the brake, further increases the activities of immune cells, making the cells more effective in killing tumor cells, and ultimately achieving more effective therapeutical effects on a broader spectrum of tumors.

It has been found in recent researches that various tumor-infiltrating T cells express OX40, and that OX40-positive tumor patients have a relatively longer survival time, suggesting OX40 plays a role in tumor immunity. In many preclinical animal models, the activation of OX40 led to stimulated T cells proliferation, enhanced effector T cells function, and inhibition of the function of regulatory T cells. In a clinical trial using OX40 agonist (9B12) to treat patients with metastatic solid tumors, it was seen that the immune functions improved in cancer patients, with regression of at least one metastatic lesion in 12 out of 30 patients, and that the OX40 antibody was well tolerated in the treated patients. Currently, agonistic OX40 monoclonal antibodies (e.g. MOXR0916, PF-04518600, BMS 986178, GSK3174998, MEDI0562, MEDI6469, and MEDI6383) are being evaluated in several clinical trials either as monotherapy or in combination with other immunomodulating agents.

Autoimmune diseases are another major medical challenge confronting humans today, and OX40 inhibitors are expected to be a potential treatment for autoimmune diseases. In a pre-clinical study, it has been shown that OX40 or OX40L deficient mice exhibit significantly decreased Th2 cell function in mouse models of allergic asthma. OX40 inhibitors can relieve symptoms associated with suppression of the T cell function in the asthma model mice. Similar results were observed in monkey in vivo studies. In addition, immunosuppression and symptom relief after blocking OX40-OX40L signaling pathway are also seen in other classic models of inflammation and autoimmune diseases, including models such as experimental allergic encephalomyelitis model (EAE), rheumatoid arthritis model (RA), as well as colitis model, graft-versus-host disease model, type I diabetes model, in which $CD4^+$ or $CD8^+$ T cells play key roles. In regard to OX40 antagonist antibodies, the current clinical trials have achieved preliminary results. GRB830 is a humanized human IgG1 monoclonal antibody developed by Glenmark Pharmaceuticals Inc., it blocks the binding of OX40 to OX40L by binding to the second cysteine-rich domain of OX40, thereby inhibiting T cell activation caused by OX40L. GBR830 has demonstrated positive results in an ongoing clinical trial for moderate and severe atopic dermatitis (Phage IIa, NCT 02683928). In addition, OX40 antagonist monoclonal antibody KHK4083 developed by Japan Company Kyowa Hakko showed good tolerance and efficacy in a phase I clinical trial for atopic dermatitis, and the phase II clinical trial of the drug (NCT 03703102) for moderate and severe atopic dermatitis was initiated on October, 2018.

So far, no anti-OX40 antibody with a clear efficacy has been approved for the treatment of any human disease. It is of great significance to further develop such drugs to meet the huge clinical needs.

SUMMARY OF THE INVENTION

The present invention provides an anti-OX40 antibody or antigen-binding fragment thereof, and methods for preparing and using same, including a method for treating OX40-related diseases or conditions.

In one aspect, the present invention provides an isolated anti-OX40 antibody or antigen-binding fragment thereof, comprising one to three selected from HCDR1, HCDR2 and HCDR3 of a heavy chain variable region (VH), wherein the amino acid sequence of the VH is as set forth in SEQ ID NO: 1, 2, 3, 4 or 5.

In one aspect, the present invention provides an isolated anti-OX40 antibody or antigen-binding fragment thereof, comprising one to three selected from LCDR1, LCDR2 and LCDR3 of a light chain variable region (VL), wherein the amino acid sequence of the VL is as set forth in SEQ ID NO: 6, 7, 8, 9 or 10.

In some embodiments, the present invention provides an isolated OX40 antibody or antigen-binding fragment thereof, which comprises three CDRs of a heavy chain variable region (VH), i.e., HCDR1, HCDR2 and HCDR3, and three CDRs of a light chain variable region (VL), i.e., LCDR1, LCDR2 and LCDR3, wherein the amino acid sequence of the VH is as set forth in SEQ ID NO: 1, 2, 3, 4 or 5, and the amino acid sequence of the VL is as set forth in SEQ ID NO: 6, 7, 8, 9 or 10.

In some embodiments, the present invention provides an isolated anti-OX40 antibody or antigen-binding fragment thereof, which comprises three CDRs of a heavy chain variable region (VH), i.e., HCDR1, HCDR2 and HCDR3, and three CDRs of a light chain variable region (VL), i.e., LCDR1, LCDR2 and LCDR3; wherein the VH and VL are selected from:

(1) a VH comprising the amino acid sequence as set forth in SEQ ID NO: 1, and a VL comprising the amino acid sequence as set forth in SEQ ID NO: 6;

(2) a VH comprising the amino acid sequence as set forth in SEQ ID NO: 2, and a VL comprising the amino acid sequence as set forth in SEQ ID NO: 7 or 9;

(3) a VH comprising the amino acid sequence as set forth in SEQ ID NO: 3, and a VL comprising the amino acid sequence as set forth in SEQ ID NO: 9; or (4) a VH comprising the amino acid sequence as set forth in SEQ ID NO: 4 and a VL comprising the amino acid sequence as set forth in SEQ ID NO: 7 or 8.

In one aspect, the present invention provides an isolated anti-OX40 antibody or antigen-binding fragment thereof, comprising one to three of heavy chain complementary determining regions (HCDRs), HCDR1, HCDR2 and HCDR3, wherein the HCDR1 comprises the amino acid sequence as set forth in SEQ ID NO: 11, the HCDR2 comprises the amino acid sequence as set forth in SEQ ID NO: 12, and the HCDR3 comprises the amino acid sequence as set forth in SEQ ID NO: 13.

In one aspect, the present invention provides an isolated anti-OX40 antibody or antigen-binding fragment thereof, comprising one to three of light chain complementary determining regions (LCDRs), LCDR1, LCDR2 and LCDR3, wherein the LCDR1 comprises the amino acid sequence as set forth in SEQ ID NO: 14, the LCDR2 comprises the amino acid sequence as set forth in SEQ ID NO: 15, and the LCDR3 comprises the amino acid sequence as set forth in SEQ ID NO: 16.

In some embodiments, the anti-OX40 antibody or antigen-binding fragment thereof provided by the present invention comprises heavy chain complementary determining regions (HCDRs), HCDR1, HCDR2 and HCDR3, and light chain complementary determining region s (LCDRs), LCDR1, LCDR2 and LCDR3, wherein the HCDR1 comprises the amino acid sequence as set forth in SEQ ID NO: 11, the HCDR2 comprises the amino acid sequence as set forth in SEQ ID NO: 12, the HCDR3 comprises the amino acid sequence as set forth in SEQ ID NO: 13, the LCDR1 comprises the amino acid sequence as set forth in SEQ ID NO: 14, the LCDR2 comprises the amino acid sequence as set forth in SEQ ID NO: 15 and the LCDR3 comprises the amino acid sequence as set forth in SEQ ID NO: 16.

In some embodiments, the anti-OX40 antibody or antigen-binding fragment thereof provided by the present invention comprises a heavy chain variable region (VH), wherein the VH comprises the amino acid sequence identical to or having at least 90%, 91%, 92%, 93%, 94%, 95%, 96%, 97%, 98% or 99% sequence identity to the amino acid sequence as set forth in SEQ ID NO: 1, 2, 3, 4 or 5.

In some embodiments, the anti-OX40 antibody or antigen-binding fragment thereof provided by the present invention comprises a light chain variable region (VL), wherein the VL comprises an amino acid sequence identical to or having at least 90%, 91%, 92%, 93%, 94%, 95%, 96%, 97%, 98% or 99% sequence identity to the amino acid sequence as set forth in SEQ ID NO: 6, 7, 8, 9 or 10.

In some embodiments, the anti-OX40 antibody or antigen-binding fragment thereof provided by the present invention comprises a heavy chain variable region (VH) and a light chain variable region (VL), wherein the VH comprises an amino acid sequence identical to or having at least 90%, 91%, 92%, 93%, 94%, 95%, 96%, 97%, 98% or 99% sequence identity to the amino acid sequence as set forth in SEQ ID NO: 1, wherein the VL comprises an amino acid sequence identical to or having at least 90%, 91%, 92%, 93%, 94%, 95%, 96%, 97%, 98% or 99% sequence identity to the amino acid sequence as set forth in SEQ ID NO: 6.

In some embodiments, the anti-OX40 antibody or antigen-binding fragment thereof provided by the present invention comprises a heavy chain variable region (VH) and a light chain variable region (VL), wherein the VH comprises an amino acid sequence identical to or having at least 90%, 91%, 92%, 93%, 94%, 95%, 96%, 97%, 98% or 99% sequence identity to the amino acid sequence as set forth in SEQ ID NO: 2, 3, 4, or 5, wherein the VL comprises an amino acid sequence identical to or having at least 90%, 91%, 92%, 93%, 94%, 95%, 96%, 97%, 98% or 99% sequence identity to the amino acid sequence as set forth in SEQ ID NO: 7, 8, 9 or 10.

In some embodiments, the anti-OX40 antibody or antigen-binding fragment thereof provided by the present invention comprises a heavy chain variable region (VH) and a light chain variable region (VL), wherein the VH comprises the amino acid sequence as set forth in SEQ ID NO: 1, and wherein the VL comprises the amino acid sequence as set forth in SEQ ID NO: 6.

In some embodiments, the anti-OX40 antibody or antigen-binding fragment thereof provided by the present invention comprises a heavy chain variable region (VH) and a light chain variable region (VL), wherein the VH comprises the amino acid sequence as set forth in SEQ ID NO: 2, 3, 4 or 5, and wherein the VL comprises the amino acid sequence as set forth in SEQ ID NO: 7, 8, 9 or 10.

In some embodiments, the anti-OX40 antibody or antigen-binding fragment thereof provided by the present invention comprises a heavy chain variable region (VH) and a light chain variable region (VL), wherein the VH comprises the amino acid sequence as set forth in SEQ ID NO: 2, and wherein the VL comprises the amino acid sequence as set forth in SEQ ID NO: 7.

In some embodiments, the anti-OX40 antibody or antigen-binding fragment thereof provided by the present invention comprises a heavy chain variable region (VH) and a light chain variable region (VL), wherein the VH comprises the amino acid sequence as set forth in SEQ ID NO: 2, and wherein the VL comprises the amino acid sequence as set forth in SEQ ID NO: 9.

In some embodiments, the anti-OX40 antibody or antigen-binding fragment thereof provided by the present invention comprises a heavy chain variable region (VH) and a light chain variable region (VL), wherein the VH comprises the amino acid sequence as set forth in SEQ ID NO: 3, and wherein the VL comprises the amino acid sequence as set forth in SEQ ID NO: 9.

In some embodiments, the anti-OX40 antibody or antigen-binding fragment thereof provided by the present invention comprises a heavy chain variable region (VH) and a light chain variable region (VL), wherein the VH comprises the amino acid sequence as set forth in SEQ ID NO: 4, and wherein the VL comprises the amino acid sequence as set forth in SEQ ID NO: 7.

In some embodiments, the anti-OX40 antibody or antigen-binding fragment thereof provided by the present invention comprises a heavy chain variable region (VH) and a light chain variable region (VL), wherein the VH comprises the amino acid sequence as set forth in SEQ ID NO: 4, and wherein the VL comprises the amino acid sequence as set forth in SEQ ID NO: 8.

In some embodiments, the anti-OX40 antibody or antigen-binding fragment thereof provided by the present invention is a murine antibody, a chimeric antibody or a humanized antibody. In some embodiments, the present invention provides an anti-OX40 antibody or antigen-binding fragment thereof, which is a full-length antibody, a single-domain antibody (such as a VHH), a Fab, a Fab', a Fab'-SH, a (Fab')2, a single-chain antibody (such as a scFv), a Fv, a dAb (domain antibody) or a bis(multi)-specific antibody.

In some embodiments, the anti-OX40 antibody or antigen-binding fragment thereof provided by the present invention comprises an Fc region. In some embodiments, the amino acid sequence of the Fc region is identical to the sequence of the Fc region of human IgG1, IgG2 or IgG4, or is a variant thereof.

In another aspect, the present invention provides an anti-OX40 antibody agonist, comprising the CDRs of the antibody provided by the present invention and an Fc region binding to FcγR. In some embodiments, the amino acid sequence of the Fc region of the anti-OX40 antibody agonist is identical to the amino acid sequence of the Fc region of human IgG1 or IgG2.

In another aspect, the present invention provides an anti-OX40 antibody antagonist, comprising the CDRs of the antibody provided by the present invention. In some embodiments, the anti-OX40 antibody antagonist comprises an Fc region variant, which variant reduces or eliminates the binding of the Fc region to FcγR. In some embodiments, the anti-OX40 antibody antagonist comprises an Fc region variant, which variant is human IgG1 N297A.

In a preferable embodiment, the present invention provides an isolated anti-OX40 antibody, comprising (1) heavy chain complementary determining regions (HCDRs), HCDR1, HCDR2 and HCDR3, wherein the HCDR1 comprises the amino acid sequence as set forth in SEQ ID NO: 11, the HCDR2 comprises the amino acid sequence as set forth in SEQ ID NO: 12, and the HCDR3 comprises the amino acid sequence as set forth in SEQ ID NO: 13;

(2) light chain complementary determining regions (LCDRs), LCDR1, LCDR2 and LCDR3, wherein the LCDR1 comprises the amino acid sequence as set forth in SEQ ID NO: 14, the LCDR2 comprises the amino acid sequence as set forth in SEQ ID NO: 15, and the LCDR3 comprises the amino acid sequence as set forth in SEQ ID NO: 16; and (3) a Fc region variant, which is human IgG1 N297A. Preferably, the binding of the Fc region variant to FcγR is reduced or eliminated. In an embodiment, the antibody comprises a heavy chain variable region (VH) and a light chain variable region (VL), wherein the VH comprises the amino acid sequence as set forth in SEQ ID NO: 2, and wherein the VL comprises the amino acid sequence as set forth in SEQ ID NO: 7. In one embodiment, the antibody is a full-length antibody. In another embodiment, the antibody has a binding affinity ($K_D$) for human OX40 of less than 10 nM. In another embodiment, the antibody is an OX40 antibody antagonist and has an activity for blocking OX40-mediated signal transduction.

In another aspect, the present invention provides an isolated nucleic acid, which encodes any of the antibodies or fragment thereof provided by the present invention, wherein preferably, the nucleic acid encodes the heavy chain or the light chain, or the heavy chain variable region or the light chain variable region of the antibody of the present invention.

In another aspect, the present invention provides a recombinant vector or an expression vector, comprising one or more nucleic acids provided by the present invention, wherein the vector is suitable for recombinant production of any antibody or antigen-binding fragment thereof provided by the present invention. In some embodiments, the vector is an expression vector.

In another aspect, the present invention provides a host cell, comprising one or more nucleic acids, or recombinant vectors or expression vectors provided by the present invention.

In another aspect, the present invention provides an immunoconjugate or immune fusion, comprising the anti-OX40 antibody or antigen-binding fragment thereof provided by the present invention.

In another aspect, the present invention provides a pharmaceutical composition, comprising the anti-OX40 antibody or antigen-binding fragment thereof, the nucleic acid, the vector or the host cell provided by the present invention, and optionally comprising at least one pharmaceutically acceptable auxiliary substance, such as a pharmaceutical carrier or a pharmaceutical excipient.

In another aspect, the present invention also provides the use of the anti-OX40 antibody or antigen-binding fragment thereof, the nucleic acid, the vector, the host cell, the immunoconjugate or the immune fusion provided by the present invention, in the preparation of drugs for treating OX40-related diseases or conditions.

In another aspect, the present invention also provides the use of the anti-OX40 antibody agonist of the present invention in the preparation of drugs for treating cancers.

In another aspect, the present invention also provides the use of the anti-OX40 antibody antagonist of the present invention in the preparation of drugs for treating inflammation and/or autoimmune diseases.

In another aspect, the present invention provides a method for treating or preventing an OX40-related disease or condition, comprising administering to a subject an effective amount of the antibody or antigen-binding fragment thereof, or the nucleic acid, the vector, the host cell, the immunoconjugate or the immune fusion, or the pharmaceutical composition comprising same provided by the present invention. In some embodiments, wherein the OX40-related disease or condition is inflammation and/or autoimmune disease, such as graft-versus-host disease. In some embodiments, wherein the OX40-related disease or condition is cancers, such as melanoma, preferably metastatic melanoma.

The anti-OX40 antibody or antigen-binding fragment thereof of the present invention can also be combined with other therapeutic agents or procedures, for treating or preventing OX40-related diseases or conditions.

In another aspect, the present invention also provides a method for detecting OX40 in a sample by using the anti-OX40 antibody or antigen-binding fragment thereof of the present invention. The method can be used to diagnose/detect OX40-related diseases or conditions.

The present invention also encompasses any combinations of any embodiments described herein. Any embodiments or any combinations thereof described herein are applicable to any and all anti-OX40 antibodies or fragments, methods and uses thereof of the present invention described herein.

DETAILED DESCRIPTION OF THE INVENTION

Figure 1:
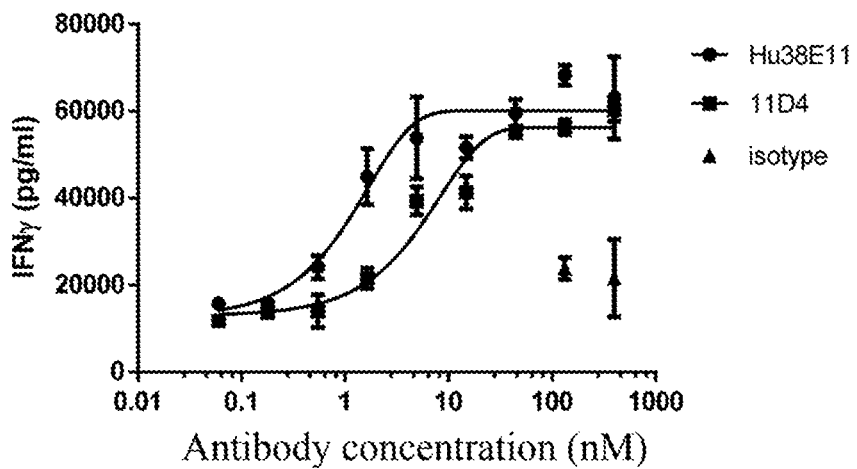
FIG. 1 shows that Hu38E11-IgG2 antibody enhances the secretion of IFNγ by human T cells activated with an anti-CD3 antibody.

The present invention provides an anti-OX40 antibody or antigen-binding fragment thereof, having a unique CDR sequence, and having high affinity and specificity for binding to human OX40. The anti-OX40 antibody or antigen-binding fragment thereof provided by the present invention can be used alone or in combination with other therapies for the treatment of diseases or conditions, such as cancers, inflammation or autoimmune diseases.

Definitions

Unless otherwise stated, the present invention will be implemented using conventional techniques in molecular biology (including recombinant techniques), microbiology, cell biology, biochemistry and immunology, which are within the skill of the art.

In order that the present invention may be more readily understood, some scientific and technical terms are defined as follows. Unless otherwise explicitly defined herein, all scientific and technical terms used herein have the same meaning as commonly understood by those of ordinary skill in the art to which the present invention pertains. For definitions and terminology in the art, specific reference can be made to Current Protocols in Molecular Biology (Ausubel) by professionals. The abbreviations of amino acid residues are the standard 3-letter and/or 1-letter codes used for any one of the 20 L-amino acids commonly used in the art. The singular forms, "a", "an" and "the", used in the present application and the appended claims include plural forms, unless otherwise specified in the context clearly.

The term "about" means a value or an integer within an acceptable error range for the particular value or integer as determined by one of ordinary skill in the art, which depends in part on how the value or composition is measured or determined, i.e., the limitations of the measurement system. For example, "about" can refer to within 1 or more than 1 standard deviation per the practice in the art. Alternatively, "about" can refer to a range of up to 5%, 10% or 20% (i.e., ±5%, ±10% or ±20%).

When used to connect two or more optional items, the term "and/or" should be understood to mean any one of the optional items or any two or more of the optional items.

As used herein, the term "comprise" or "include" means to include the mentioned elements, integers, or steps, but does not exclude any other elements, integers, or steps. As used herein, the term "comprise" or "include", unless otherwise indicated, encompasses "consisting of" the mentioned elements, integers or steps. For example, when referring to an antibody variable region "comprising" a specific sequence, it is also intended to encompass an antibody variable region consisting of the specific sequence.

The term "OX40" herein refers to a type I transmembrane glycoprotein of about 50 KD, which is a member of tumor necrosis factor receptor superfamily. OX40 is also referred to as ACT35, CD134 or TNFRSF4. As used herein, the term refers to any natural OX40 from any vertebrate source, including mammals such as primates (e.g., humans) and rodents (e.g., mice and rats), unless otherwise stated. The term encompasses a "full length", unprocessed OX40 and any form of OX40 or any fragment thereof due to processing in the cell. The term also includes naturally occurring variants of OX40, such as splice variants or allelic variants. In some embodiments, OX40 refers to a full length OX40 from human, or a fragment thereof (such as the mature fragment lacking a signal peptide). In some embodiments, a human OX40 refers to a mature OX40 identical to the amino acid sequence as set forth under the accession number Uniprot #P43489 (amino acid residues 1-28 being the leader peptide), or a fragment thereof (such as an extracellular domain thereof). In some embodiments, the term also covers a fusion protein comprising OX40 or a fragment thereof (such as an extracellular domain thereof), such as a fusion protein comprising a human OX40 extracellular domain and an Fc region.

The term "OX40 ligand" or "OX40L" as used herein refers to the unique ligand of OX40, also referred to as gp34, CD252 or TNFSF4. A human OX40 ligand is identical to the amino acid sequence as set forth under the accession number uniprot #P23510, or is a variant thereof. OX40L naturally forms a homotrimer on a cell surface, and is mainly expressed on activated antigen presenting cells (APC), including activated B cells, mature conventional dendritic cells (DC), plasmacytoid dendritic cells (pDC), macrophages and Langerhans cells, and can be expressed on other cell types, such as NK cells, mast cells, a subset of activated T cells, and vascular endothelial cells and smooth muscle cells.

The term "affinity" as used herein refers to the strength of the sum of all noncovalent interactions between a single binding site of a molecule (e.g., an antibody) and its binding partner (e.g., an antigen). Unless otherwise indicated, as used herein, "binding affinity" refers to the intrinsic binding affinity which reflects a 1:1 interaction between members of a binding pair (e.g., an antibody and an antigen). The affinity of molecule X for its partner Y is generally expressed by the dissociation constant ($K_D$). Methods for determining binding affinity are known in the art, including surface plasmon resonance (e.g., BIACORE) or similar techniques (e.g., ForteBio).

The terms "OX40 antagonist", "OX40 inhibitor", "OX40 antagonist antibody", "antagonist OX40 antibody" and "OX40 antibody antagonist", are used interchangeably herein. These terms include antibodies capable of inhibiting and/or neutralizing OX40-mediated biological signal transduction activity. In some embodiments, an OX40 antagonist antibody inhibits or suppresses the signal transduction pathway triggered by OX40, and/or inhibits or reduces an OX40-mediated cellular response such as lymphocyte proliferation, cytokine expression or lymphocyte survival, for example by blocking the binding of OX40 to an OX40 ligand or substantially reducing the binding of OX40 to an OX40 ligand.

The terms "OX40 agonist", "OX40 agonist antibody", "OX40 agonistic antibody" and "OX40 antibody agonist" are used interchangeably herein. These terms include antibodies capable of promoting and/or enhancing OX40-mediated biological signal transduction activity. In some embodiments, an OX40 agonist antibody promotes or enhances the signal transduction pathway triggered by OX40, and/or promotes or enhances an OX40-mediated cell response such as lymphocyte proliferation, cytokine expression or lymphocyte survival, for example, by cross-linking and binding to OX40 and activating OX40-mediated biological signal.

The term "OX40-related disease or condition" as used herein refers to a non-physiological state related to the expression or function or activity of OX40, or to the activity of OX40-mediated signal transduction, including but not limited to cancers, inflammation and autoimmune diseases. In some embodiments, the diseases will benefit from the blocking of OX40-mediated signal transduction. In some embodiments, the diseases will benefit from the activation of OX40-mediated signal transduction.

The terms "immune response" and "immune reaction" are used interchangeably herein and refer to the action of, such as lymphocytes, antigen presenting cells, phagocytes and granulocytes, and soluble macromolecules produced by the above cells or the liver (including antibodies, cytokines and complements) that results in the selective damage, destruction or elimination of invading pathogens, cells or tissues infected with pathogens, cancer cells, or in the case of autoimmunity or pathological inflammation, normal human cells or tissues, from the human body. In some embodiments, the OX40 antibody antagonist of the present invention inhibits or reduces immune reaction, for example, reduces immune rejection in graft-versus-host diseases. In some embodiments, the OX40 antibody agonist of the present invention enhances an anti-tumor immune reaction.

The term "signal transduction" as used herein refers to a biochemical causal relationship generally initiated by a protein-protein interaction such as binding of OX40L (ligand) to OX40 (receptor), resulting in the transmission of a signal from one part of a cell to another part of a cell. Generally, the transmission involves the specific phosphorylation of one or more tyrosine, serine, or threonine residues on one or more proteins in a series of reactions that cause the signal transduction. The penultimate process generally includes nuclear events, thereby causing changes in gene expression.

The phrase "enhancing T cell function" or "T-cell agonistic activity" as used herein includes inducing, triggering or stimulating the renewal of effector or memory T cells, and/or maintaining or amplifying, and/or inducing, triggering or stimulating the biological function of effector or memory T cells. Examples of enhancing the function of a T cell include: relative to such levels before intervention, elevated secretion of gamma interferon (INF-γ) from $CD8^+$ effector T cells, elevated secretion of gamma interferon (INF-γ) from CD4+ memory T cells and/or effector T cells, elevated proliferation of CD4+ effector T cells and/or memory T cells, elevated CD8+ effector T cell proliferation, and elevated antigen responsiveness (e.g., clearance). In one embodiment, relative to pre-intervention, the level is increased by at least 50%, or 60%, 70%, 80%, 90%, 100%, 120%, 150%, 200%, 300%, 500% or more. The manner of measuring this enhancement is known to a person of ordinary skill in the art. In some embodiments, the T-cell agonistic activity of the antibody of the present invention is evaluated by detecting inflammatory factor IFNγ released by activated T cells in the presence of the antibody of the present invention. In some embodiments, the EC50 value that promotes T cells to release IFNγ is determined for the antibody of the present invention, wherein a lower value indicates that the antibody has a higher T-cell agonistic activity. In some embodiments, the antibody of the present invention has a higher T-cell agonistic activity compared to a reference OX40 agonist antibody (e.g., OX40mAb24).

The phrase "reducing T cell function" or "T-cell antagonistic activity" as used herein includes reducing, blocking, or decreasing the renewal of effector or memory T cells, and/or reducing, blocking, or decreasing the biological function of effector or memory T cells. Examples of reducing T-cell function include: relative to such levels before intervention, reduced secretion of gamma interferon (INF-γ) from $CD8^+$ effector T cells, reduced secretion of gamma interferon (INF-γ) from CD4+ memory and/or effector T cells, reduced proliferation of CD4+ effector T cells and/or memory T cells, reduced CD8+ effector T cell proliferation, and reduced antigen responsiveness (e.g., clearance). In one embodiment, relative to pre-intervention, the level is decreased by at least 50%, or 60%, 70%, 80%, 90%, 100%, 120%, 150%, 200%, 300%, 500% or more. The manner of measuring this reduction is known to a person of ordinary skill in the art. In some embodiments, the T-cell antagonistic activity of the antibody of the present invention is evaluated by detecting inflammatory factor IFNγ released by activated T cells in the presence of OX40 ligand OX40L and the antibody of the present invention. In some embodiments, the $IC_{50}$ value that blocks OX40-OX40L mediated IFNγ release from T cells is determined for the antibody of the present invention, wherein a lower value indicates that the antibody has a higher antagonistic activity. In some embodiments, the antibody of the present invention has a higher T-cell antagonistic activity compared to a reference OX40 antagonist antibody (e.g., GBR830).

The terms "activity" and "biological activity" or the terms "biological property" and "biological feature" as used herein are used interchangeably herein and include, but not limited to, epitope/antigen affinity and specificity, ability to neutralize or antagonize an OX40 activity in vivo or in vitro, ability to enhance or activate OX40 in vivo or in vitro, T-cell agonistic activity, $IC_{50}$ that blocks the binding of OX40 to OX40L, $IC_{50}$ that blocks OX40-OX40L-mediated T cell activation, in vivo stability of an antibody and immunogenicity of an antibody. Other identifiable biological properties or features of antibodies known in the art include, for example, cross reactivity (i.e., cross reactivity, generally with non-human homologs of targeted peptides, or with other proteins or tissues), and the ability to maintain high levels of antibody expression in mammalian cells. The properties or features mentioned above can be observed, determined or evaluated using techniques well known in the art, including but not limited to ELISA, FACS or BIACORE plasmon resonance assay, in vitro or in vivo neutralization assay, receptor binding, production and/or secretion of cytokines or growth factors, signal transduction and immunohistochemistry of tissue sections from different sources (including humans, primates, or any other sources).

The term "antibody" as used herein refers to any form of antibody having a desirable bioactivity. Therefore, it is used in the broadest sense, including but not limited to a monoclonal antibody (including a full-length monoclonal antibody), a polyclonal antibody, a multispecific antibody (such as a bispecific antibody), a humanized antibody, a fully human antibody, a chimeric antibody, a CrossMab antibody, or a camelized single-domain antibody.

The terms "whole antibody", "full-length antibody" and "intact antibody" are used interchangeably herein and refer to a glycoprotein comprising at least two heavy chains (H) and two light chains (L) interconnected by disulfide bonds. Each heavy chain consists of a heavy chain variable region (hereinafter abbreviated as VH) and a heavy chain constant region. The heavy chain constant region consists of 3 domains CH1, CH2 and CH3. Each light chain consists of a light chain variable region (hereinafter abbreviated as VL) and a light chain constant region. The light chain constant region consists of one domain CL. The VH region and VL region can be further divided into hypervariable regions (termed complementary determining region (CDR)), interspersed with more conservative regions (termed framework region (FR)). A "complementary determining region" or "CDR region" or "CDR" is a region in an antibody variable domain, which is hypervariable in sequence and forms a structurally defined loop ("hypervariable loop") and/or contains antigen-contacting residues ("antigen contact sites"). CDR is mainly responsible for binding to epitopes. CDRs of heavy chain and light chain are generally called CDR1, CDR2 and CDR3, which are numbered sequentially from the N-terminus. The CDRs located in an antibody heavy chain variable domain are called HCDR1, HCDR2 and HCDR3 respectively, while the CDRs located in the antibody light chain variable domain are called LCDR1, LCDR2 and LCDR3 respectively. Each VH or VL consists of three CDRs and 4 FRs, which are arranged in the following order from the amino terminus to the carboxyl terminus: FR1, CDR1, FR2, CDR2, FR3, CDR3, and FR4. Constant regions are not directly involved in the binding of an antibody to an antigen, but show multiple effector functions.

In a given VH or VL amino acid sequence, the accurate amino acid sequence boundary of each CDR can be determined by using any one of the various well known schemes or a combination thereof, including, for example: Chothia scheme (Chothia et al., Canonical Structures for the Hypervariable Regions of Immunoglobulins", Journal of Molecular Biology, 196, 901-917 (1987)); Kabat scheme (Kabat et al., Sequences of Proteins of Immunological Interest, 4th edition, U.S. Department of Health and Human Services, National Institutes of Health (1987)), AbM (University of Bath) and Contact (University College London); North scheme (North et al., A New Clustering of Antibody CDR Loop Conformations", Journal of Molecular Biology, 406, 228-256 (2011)). The boundary of the CDRs of the anti-OX40 antibody in the present invention can be determined according to any schemes or a combination thereof in the art and manual evaluation.

The light chains of antibodies can be assigned to one of two types (referred to as kappa (κ) and lambda (λ)) based on the amino acid sequence of the constant domain thereof. The heavy chains of antibodies can be divided into 5 major different classes according to the amino acid sequence of the heavy chain constant region thereof: IgA, IgD, IgE, IgG and IgM, and several of these classes can be further divided into subclasses, such as IgG1, IgG2, IgG3, IgG4, IgA1 and IgA2.

An "antibody in the form of IgG" means the heavy chain constant region of the antibody is of an IgG form. For example, an antibody in the form of IgG2 means that the heavy chain constant region thereof is of IgG2 isotype.

The term "antigen-binding fragment" of an antibody as used herein includes fragments or derivatives of the antibody. Generally, the antigen-binding fragment includes at least one fragment (such as one or more CDRs) of the antigen-binding region or variable region of the antibody, and maintains at least some of the binding properties of the antibody. Examples of an antigen-binding fragment include, but are not limited to Fab, Fab', F(ab')$_2$ and Fv fragments; diabodies; linear antibodies; single-chain antibody molecules (e.g., sc-Fv); and nanobodies and multispecific antibodies formed from antibody fragments. When the antigen-binding activity is expressed in molar concentration, the binding fragments or derivatives generally maintain at least 10% of the antigen-binding activity of the antibody from which they are derived. Preferably, the binding fragments or derivatives maintain at least 20%, 50%, 70%, 80%, 90%, 95% or 100% or more of the antigen binding activity of the antibody from which they are derived.

It is appreciated that an antibody or antigen-binding fragment thereof may include a conservative or non-conservative amino acid substitution that does not significantly change its biological activity (referred to as "conserved variant" or "functionally conserved variant" of the antibody). In a preferred aspect, a conservative substitution is from the exemplary conservative substitution residues shown in Table A below, and preferably, the preferred conservative amino acid substitution residues shown in Table A.

TABLE A

| Original Residue | Exemplary Substitution | Preferred conservative amino acid substitution |
| --- | --- | --- |
| Ala (A) | Val; Leu; Ile | Val |
| Arg (R) | Lys; Gln; Asn | Lys |
| Asn (N) | Gln; His; Asp; Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

An epitope is a region of an antigen that is bound by an antibody. An epitope can be formed from contiguous amino acids or non-continuous amino acids juxtaposed by tertiary folding of a protein.

The term "an isolated anti-OX40 antibody or antigen-binding fragment thereof" as used herein refers to the purified state of the anti-OX40 antibody or antigen-binding fragment thereof. For example, "isolated" may mean that the molecule is substantially free of other biomolecules, such as nucleic acids, proteins, lipids, sugars or other substances, such as cell debris and growth medium. However, as is known to a person skilled in the art, the term "isolated" is not intended to mean the complete absence of such substances, or the absence of water, buffer or salt unless they are present in an amount that substantially interferes with the experimental or therapeutic application of the antibodies described herein. In some embodiments, the isolated antibody or antigen-binding fragment has a purity of greater than 95%, greater than 96%, greater than 97%, greater than 98% or greater than 99%, as determined by, for example, electrophoresis (e.g., SDS-PAGE, isoelectric focusing (IEF), capillary electrophoresis) or chromatography (e.g., ion exchange or reverse phase HPLC). For a review of methods for assessing antibody purity, see, for example, Flatman, S. et al., J. Chrom. B 848 (2007) 79-87.

The term "monoclonal antibody" as used herein refers to an antibody obtained from a population of substantially homogeneous antibodies, i.e., the individual antibodies constituting the population are identical except for possible naturally occurring mutations that may be present in minor amounts. Monoclonal antibodies are highly specific, being directed against a single epitope. In contrast, conventional (polyclonal) antibody preparations typically include different antibodies directed against different epitopes (or specific for different epitopes). The modifier "monoclonal" indicates the feature of the antibody as being obtained from a substantially homogeneous population of antibodies, and is not to be constructed as requiring any particular method to produce the antibody.

The term "chimeric antibody" as used herein refers to an antibody having a variable domain of a first antibody and a constant domain of a second antibody, wherein the first antibody and the second antibody are from different species. Generally, the variable domain is obtained from the antibody of an experimental animal such as a rodent, while the constant domain sequence is obtained from a human antibody, so that the obtained chimeric antibody is less likely to induce adverse immune response in human subjects than the antibody from the experimental animal.

The term "humanized antibody" as used herein refers to an antibody form containing sequences from human and non-human (e.g., mouse, rat) antibodies. In general, the humanized antibody comprises at least one, and generally two, variable domains, in which all or substantially all of the hypervariable loops correspond to those of non-human immunoglobulin, and all or substantially all of the framework (FR) regions correspond to those of human immunoglobulin. The humanized antibody can optionally comprise at least a portion of a constant region (Fc) derived from a human immunoglobulin. In some cases, as is known to a person skilled in the art, amino acid mutations can be introduced into humanized antibodies (e.g., variable domains, framework regions, and/or constant regions (if present)), for example, to improve certain properties of the antibodies; such antibody forms still fall within the scope of the "humanized antibody" of the present invention.

As is known to a person skilled in the art, an antibody may have a sugar chain found in the cells for producing the antibody. For example, when produced in mice, in mouse cells, or in hybridomas derived from mouse cells, the antibody may contain a mouse sugar chain. Alternatively, when produced in rats, in rat cells, or in hybridomas derived from rat cells, the antibody may contain a rat sugar chain.

The term "Fc region" as used herein is used to define the C-terminal region of an immunoglobulin heavy chain that comprises at least a portion of the constant region. The term includes native sequence Fc regions and variant Fc regions. The native-sequence Fc region covers a variety of naturally occurring immunoglobulin Fc sequences, such as various Ig subtypes and allogeneic Fc regions thereof (Gestur Vidarsson et al., IgG subclasses and allotypes: from structure to effector functions, 20 Oct. 2014, doi: 10.3389/fimmu.2014.00520). In one embodiment, the Fc region of the human IgG heavy chain extends from Cys226 or from Pro230 to the carboxyl terminus of the heavy chain. However, the lysine at the C-terminus (Lys447) of Fc region may or may not be present. Unless otherwise specified herein, amino acid residues in Fc region or constant region are numbered in accordance with the EU numbering system, also referred to EU index, as described in Kabat et al., Sequences of Proteins of Immunological Interest, 5th edition Public Health Service, National Institutes of Health, Bethesda, Md., 1991.

The terms "Fc region variant" and "variant Fc region" as used herein are used interchangeably herein, and refer to an Fc region polypeptide comprising an amino acid modification(s) relative to a native sequence Fc region. The Fc region variants of the present invention are defined according to the amino acid modifications that compose them. Thus, for example, N297A is an Fc region variant with the substitution of asparagine with alanine at position 297 relative to the parent polypeptide, where the number is in accordance with EU index. For example, a human IgG1 N297A refers to an Fc region variant having the sequence of an Fc region of human IgG1 with the substitution N297A. The modifications can be an addition, deletion or substitution. Substitutions can include naturally occurring amino acids and non-naturally occurring amino acids. The variant may contain non-natural amino acids.

The term "Fc receptor" or "FcR" as used herein describes a receptor that binds to an antibody Fc region. In some embodiments, FcR is a native sequence human FcR. In some embodiments, FcR is FcγR (a gamma receptor), including receptors of FcγRI, FcγRII, and FcγRIII subclasses, and also including allelic variants and alternative splicing forms of those receptors. FcγRII includes FcγRIIA (an "activating receptor") and FcγRIIB (an "inhibitory receptor"), which have similar amino acid sequences and differ primarily in the cytoplasmic domains thereof. Activating receptor FcγRIIA contains an immunoreceptor tyrosine-based activation motif (ITAM) in its cytoplasmic domain. The inhibitory receptor FcγRIIB contains an immunoreceptor tyrosine-based inhibitory motif (ITIM) in its cytoplasmic domain (see, for example, Annu. Rev. Immunol. 15: 203-234 (1997)). For a review of FcR, see, e.g., Ravetch and Kinet, Annu. Rev. Immunol. 9: 457-492 (1991); Capel et al., Immunomethods 4: 25-34 (1994); and de Haas et al., J. Lab. Clin. Med. 126: 330-41 (1995). Other FcRs, including those to be identified in the future, are encompassed by the term "FcR" herein. The term "Fc receptor" or "FcR" also includes neonatal receptor, FcRn, which is responsible for transferring maternal IgGs to the fetus (Guyer et al., J. Immunol. 117: 587 (1976) and Kim et al., J. Immunol. 24: 249 (1994)) and regulating the homeostasis of immunoglobulins. Methods of measuring the binding of FcRn are known (see for example Ghetie and Ward, Immunol. Today 18 (12): 592-598 (1997); Ghetie et al., Nature Biotechnology, 15 (7): 637-640 (1997); Hinton et al., J. Biol. Chem. 279 (8): 6213-6216 (2004); WO 2004/92219 (Hinton et al.)). The in vivo binding to human FcRn and the serum half-life of a polypeptide with a high binding affinity for a human FcRn can be determined, for example, in transgenic mice or transfected human cell lines expressing a human FcRn, or in primates administered with a polypeptide with a variant Fc region. WO 2000/42072 (Presta) describes antibody variants with improved or reduced binding to FcRs. See, also, for example, Shields et al., J. Biol. Chem. 9 (2): 6591-6604 (2001).

The term "pharmaceutically acceptable auxiliary substance" refers to a diluent, an adjuvant (e.g., Freund's adjuvant (complete and incomplete)), a pharmaceutical excipient, a pharmaceutical carrier or a stabilizer, etc., which is administrated with an active substance.

The term "pharmaceutical composition" refers to such a composition that exists in a form that allows the biological activity of the active ingredient contained therein to be effective and does not contain additional ingredients that have unacceptable toxicity to the subject to whom the composition is administrated.

As used herein, an "immunoconjugate" is an antibody conjugated to one or more other substances, including but not limited to cytotoxic agents or labels. An "immune fusion" is an antibody which is fused by covalently linking to one or more other peptides or polypeptides.

The term "therapeutic agent" as described herein covers any substances that are effective in the prevention or treatment of related diseases, such as cancers.

The term "cytotoxic agent" as used in the present invention refers to a substance that inhibits or prevents a cellular function and/or causes cell death or destruction.

"Chemotherapeutic agents" include chemical small molecule drugs that are useful in the treatment of cancers or immune system diseases.

The term "small molecule drug" refers to a compound with a low molecular weight that can regulate biological processes. A "small molecule" is defined as a molecule with a molecular weight smaller than 10 kD, typically smaller than 2 kD and preferably smaller than 1 kD. The small molecules include but are not limited to inorganic molecules, organic molecules, organic molecules containing an inorganic component, molecules containing a radioactive atom, synthetic molecules, peptide mimics and antibody mimics. As therapeutic agents, small molecules are better able to penetrate cell membranes than large molecules, are less susceptible to degradation, and are less likely to trigger an immune response.

The term "immunomodulator" as used herein refers to a natural or synthetic active agent or drug that modulates (e.g., suppresses or enhances) an immune response. The immune response can be a humoral response or a cellular response. In some instances, an immunomodulator includes an immunosuppressant that inhibits an immune response, for example, an immunosuppressant that beneficially inhibits an immune response in inflammation and autoimmune diseases. In another instances, an immunomodulator includes an active agent or a drug that enhances an immune response, for example, an active agent or a drug that beneficially enhances an anticancer immune response in cancer treatment.

The terms "cancerous" and "cancer" refer to or describe physiological disorders in mammals, generally characterized by unregulated cell growth. This definition includes benign and malignant tumors and dormant tumors or micrometastasis. The "cancer" includes, but is not limited to, solid tumors and blood cancers. Examples of various cancers include, but are not limited to, carcinoma, lymphoma, blastoma, sarcoma and leukemia.

"Inflammation and/or autoimmune diseases" are meant to broadly include any inflammatory or immune-related conditions (e.g., pathological inflammation and autoimmune diseases). "Autoimmune diseases" are diseases or conditions that are caused by and target an individual's own tissues or organs, or co-segregated disorders or manifestations thereof or conditions arising therefrom. Autoimmune diseases may refer to conditions that are caused or exacerbated by the generation of B cells that produce antibodies reactive with normal body tissues and antigens. Autoimmune diseases may also be diseases that involve the secretion of autoantibodies specific to epitopes derived from self-antigens (e.g., nuclear antigens).

The term "vector" as used herein refers to any recombinant polynucleotide constructs that can be used for the purpose of transformation (i.e. introduction of heterologous DNA into host cells). One type of vectors is a "plasmid", a circular double stranded DNA loop, into which an additional DNA segment can be ligated. Another type of vectors is a viral vector, in which an additional DNA segment can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. In addition, some vectors can guide the expression of genes that are operably linked. Such vectors are referred to as "expression vector" herein. The expression vector refers to the nucleic acid that can replicate and express a target gene when the vector is transformed, transfected or transduced into a host cell. The expression vector comprises one or more phenotypic selectable markers and origins of replication to ensure vector maintenance and provide amplification in the host if necessary.

The term "subject" or "patient" or "individual" herein includes any human or non-human animals. The term "non-human animal" includes all vertebrates, such as mammals and non-mammals, such as non-human primates, sheep, dogs, cats, horses, bovine, chicken, amphibians, reptiles, etc.

The terms "therapeutically effective amount", "therapeutically effective dose" and "effective amount" herein refer to the amount of the anti-OX40 antibody or antigen-binding fragment thereof of the present invention that effectively prevents or improves the symptoms of one or more diseases or conditions or the development of the diseases or conditions when given to cells, tissues or subjects alone or in combination with other therapeutic drugs. Therapeutically effective dose also refers to the amount of the antibody or antigen-binding fragment thereof that is sufficient to result in improvement of the symptoms, such as the amount to treat, cure, prevent or improve related medical conditions or to increase the speed of treatment, cure, prevention or improvement of such conditions. When the active ingredient alone is administered to an individual, the therapeutically effective dose refers only to the ingredient. When administered in combination, the therapeutically effective dose refers to the total amount of active ingredients contributing to therapeutic effects, regardless of administration in combination, in sequence or at the same time. The effective amount of the therapeutic agent will result in an improvement in the diagnostic criteria or parameter by at least 10%, typically at least 20%, preferably at least about 30%, more preferably at least 40%, and most preferably at least 50%.

As used herein, "to treat" or "treating" or "treatment" includes 1) therapeutic measures, which cure, alleviate and relieve the symptoms of a diagnosed pathological condition or disease and/or stop the progression of the diagnosed pathological condition or disease, and 2) preventive or prophylactic measures, which prevent and/or slow the development of a pathological condition or disease. Therefore, the subject receiving the treatment includes an individual who has suffered from the disease, an individual who is prone to suffer from the disease, and an individual who wants to prevent the disease. In some embodiments, the present invention relates to the treatment of a disease or condition. In some other embodiments, the present invention relates to the prevention of a disease or condition.

In some embodiments according to the present invention, the "treatment" of a disease or condition refers to the improvement of the disease or condition (i.e., alleviating or preventing or reducing the progression of the disease or at least one of its clinical symptoms). In some other embodiments, "treatment" refers to relieving or improving at least one body parameter, including those physical parameters that may not be discernible by the patient. In some other embodiments, "treatment" refers to the regulation of a disease or condition physically (e.g., stabilization of a discernible symptom), physiologically (e.g., stabilization of a physical parameter), or both. Methods for evaluating the treatment and/or prevention of a disease are generally known in the art unless explicitly described herein.

In yet other embodiments according to the present invention, "prevention" of a disease or condition includes inhibition of the occurrence or development of the disease or condition or the symptom of a particular disease or condition. In some embodiments, a subject with a family history of cancer is a candidate for a prophylactic regimen. Generally, in the context of cancer, the term "prevention" refers to administration of drugs to a subject prior to the onset of conditions or symptoms of cancer, in particular, in a subject at risk of cancer.

In some embodiments, after "treating" the cancer by the method of the present invention, an individual patient is considered to have been successfully treated if the individual shows one or more of the following: the number of cancer cells is decreased or cancer cells disappear completely; tumor size is decreased; infiltration of cancer cells into peripheral organs is inhibited or absent, including, for example, the spread of cancer cells to soft tissues and bones; tumor metastasis is inhibited or absent; tumor growth is inhibited or absent; one or more symptoms associated with the specific cancer are relieved; incidence and mortality are reduced; the quality of life is improved; the tumor incidence, frequency or tumorigenicity is reduced; the number or frequency of cancer stem cells in tumor is reduced; tumor cells are differentiated into a non-tumorigenic state; or a combination of some of the effects.

"Inhibition of tumor growth" refers to any mechanism by which tumor cell growth can be inhibited. In some embodiments, tumor cell growth is inhibited by delaying tumor cell proliferation. In some embodiments, tumor cell growth is inhibited by stopping tumor cell proliferation. In some embodiments, tumor cell growth is inhibited by killing tumor cells. In some embodiments, tumor cell growth is inhibited by inducing tumor cell apoptosis. In some embodiments, tumor cell growth is inhibited by inducing tumor cell differentiation. In some embodiments, tumor cell growth is inhibited by depriving tumor cells of nutrients. In some embodiments, tumor cell growth is inhibited by preventing tumor cell migration. In some embodiments, tumor cell growth is inhibited by preventing tumor cell invasion.

As used herein, "sequence identity" refers to the degree of identity of sequences based on one by one nucleotide or amino acid comparing in the comparison window. The "(percentage) sequence identity" can be calculated as follows: comparing the two optimally aligned sequences in the comparison window, determining the number of positions with the same nucleic acid base (e.g., A, T, C, G, I) or the same amino acid residue (e.g., Ala, Pro, Ser, Thr, Gly, Val, Leu, Ile, Phe, Tyr, Trp, Lys, Arg, His, Asp, Glu, Asn, Gln, Cys and Met) in the two sequences to obtain the number of matching positions, dividing the number of matching positions by the total number of positions in the comparison window (i.e., window size), and multiplying the result by 100 to yield the percentage of sequence identity. Optimal alignment for purposes of determining the percentage of sequence identity can be achieved in various ways known in the art, for example, using publicly available computer softwares such as BLAST, BLAST-2, ALIGN or MEGA-LIGN (DNASTAR) software. Those skilled in the art is able to determine appropriate parameters for aligning sequences, including any algorithms needed to achieve maximal alignment over the full-length of the sequences or the target sequence area being compared. In the present invention, for antibody sequences, the percentage of amino acid sequence identity is determined by optimally aligning the candidate antibody sequence with the reference antibody sequence, and in a preferred embodiment in accordance with the Kabat numbering scheme.

As used herein, "GBR830" is an OX40 antagonist antibody obtained by transient expression according to VH6/VL9 heavy chain and light chain sequences disclosed in WO 2013008171; "OX40mAb24" is an OX40 agonist antibody obtained by transient expression according to heavy chain and light chain sequences of OX40mAb24 antibody disclosed in WO 2016057667; "11D4" is an OX40 agonist antibody obtained by transient expression according to heavy chain and light chain sequences of 11D4 antibody disclosed in WO 2009079335.

Anti-OX40 Antibody and Production Thereof

The antibody of the present invention can be produced by any suitable method for producing an antibody. Any suitable form of OX40 can be used as an immunogen (antigen) to produce antibodies. By way of example and not limitation, any OX40 variant or fragment thereof can be used as an immunogen. In some embodiments, hybridoma cells producing murine monoclonal anti-human OX40 antibodies may be produced by methods well-known in the art. These methods include but are not limited to the hybridoma technique originally developed by Kohler et al., (1975) (Nature 256: 495-497). Preferably, according to a standard protocol, mouse spleen cells are isolated and fused with mouse myeloma cell line by PEG or electrofusion. Then, hybridoma cells secreting an antibody with a OX40 binding activity are screened. The DNA sequences of the immunoglobulin variable regions from hybridoma cells of the present invention can be detected by the method based on a degenerate primer PCR.

Antibodies from rodents (such as mice) may cause undesired antibody immunogenicity when used as therapeutic drugs in vivo. Repeated use causes an immune response against therapeutic antibodies in humans. This kind of immune response will at least lead to the loss of therapeutic efficacy, and in severe cases, lead to potentially lethal allergic reaction. One method of reducing the immunogenicity of rodent antibodies includes the production of chimeric antibodies, in which a mouse variable region is fused with a human constant region (Liu et al. (1987) Proc. Natl. Acad. Sci. USA 84: 3439-43). However, the retention of intact rodent variable regions in chimeric antibodies may still cause harmful immunogenicity in patients.

Transplantation of CDR from a rodent variable region into a human framework (i.e., humanization) has been used to further minimize a rodent sequence. For the humanized antibody of the present invention, murine CDR regions can be inserted into a human germline framework using a method known in the art. See Winter et al., U.S. Pat. No. 5,225,539 and Queen et al., U.S. Pat. Nos. 5,530,101; 5,585,089; 5,693,762 and 6,180,370.

The accurate amino acid sequence boundary of the variable region CDR of the antibody of the present invention can be determined by using any one of many well known schemes such as Kabat, Chothia, AbM, Contact or North. It should be noted that the boundary of CDR of the variable region of the same antibody obtained by different definition systems may be different. That is, the CDR sequences of the variable region of the same antibody defined by different assignment systems are different. Therefore, when it comes to defining an antibody with a specific CDR sequence as defined in the present invention, the scope of the antibody also covers an antibody, the variable region sequence of which comprises the specific CDR sequence, but with a designated CDR boundary different from the one specified in the present invention for the specific CDR sequence, due to the application of different schemes (such as different definition systems or combinations thereof).

Antibodies with different specificities (i.e., different binding sites for different antigens) have different CDRs. However, although CDR is different from antibody to antibody, only a limited number of amino acid positions in CDR are directly involved in antigen binding. The minimum overlapping region can be determined using at least two of the Kabat, Chothia, AbM and North schemes to provide a "smallest binding unit" for antigen binding. The smallest binding unit can be a subset of CDR residues. As is appreciated by a person skilled in the art, the residues of the rest of the CDR sequence can be determined according to the structure and protein folding of the antibody. Therefore, the present invention also contemplates any variants of the CDR presented herein. In some embodiments, in a variant of CDR of the anti-OX40 antibody or antigen-binding fragment thereof of the present invention, the amino acid residues of the smallest binding unit remain unchanged, while the other CDR residues as defined according to Kabat or IMGT can be replaced by conservative amino acid residues.

In some embodiments, the present invention provides an anti-OX40 antibody or antigen-binding fragment thereof, comprising one to three selected from heavy chain complementary determining regions HCDR1, HCDR2 and HCDR3, wherein the HCDR1 comprises an amino acid sequence that is identical to the amino acid sequence as set forth in SEQ ID NO: 11 or has at least 1 and no more than 3, 2 or 1 amino acid changes (preferably amino acid substitutions, preferably conservative substitutions) compared with the amino acid sequence as set forth in SEQ ID NO: 11, the HCDR2 comprises an amino acid sequence that is identical to the amino acid sequence as set forth in SEQ ID NO: 12 or has at least 1 and no more than 3, 2 or 1 amino acid changes (preferably amino acid substitutions, preferably conservative substitutions) compared with the amino acid sequence as set forth in SEQ ID NO: 12, and the HCDR3 comprises an amino acid sequence that is identical to the amino acid sequence as set forth in SEQ ID NO: 13 or has at least 1 and no more than 3, 2 or 1 amino acid changes (preferably amino acid substitutions, preferably conservative substitutions) compared with the amino acid sequence as set forth in SEQ ID NO: 13.

In some embodiments, the present invention provides an anti-OX40 antibody or antigen-binding fragment thereof, comprising one to three selected from light chain complementary determining regions LCDR1, LCDR2 and LCDR3, wherein the LCDR1 comprises an amino acid sequence that is identical to the amino acid sequence as set forth in SEQ ID NO: 14 or has at least 1 and no more than 3, 2 or 1 amino acid changes (preferably amino acid substitutions, preferably conservative substitutions) compared with the amino acid sequence as set forth in SEQ ID NO: 14, the LCDR2 comprises an amino acid sequence that is identical to the amino acid sequence as set forth in SEQ ID NO: 15 or has at least 1 and no more than 3, 2 or 1 amino acid changes (preferably amino acid substitutions, preferably conservative substitutions) compared with the amino acid sequence as set forth in SEQ ID NO: 15, and the LCDR3 comprises an amino acid sequence that is identical to the amino acid sequence shown in SEQ ID NO: 16 or has at least 1 and no more than 3, 2 or 1 amino acid changes (preferably amino acid substitutions, preferably conservative substitutions) compared with the amino acid sequence as set forth in SEQ ID NO: 16.

In some embodiments, the present invention includes an anti-OX40 antibody or antigen-binding fragment thereof, the three HCDRs of the heavy chain variable region of which, relative to the three HCDRs specifically disclosed herein, comprise a total of at least one and no more than 5, 4, 3, 2 or 1 amino acid changes (preferably amino acid substitutions, preferably conservative substitutions), and/or the three LCDRs of the light chain variable region of which, relative to the three LCDRs specifically disclosed herein, comprise a total of at least one and no more than 5, 4, 3, 2 or 1 amino acid changes (preferably amino acid substitutions, preferably conservative substitutions).

In some embodiments, the present invention includes an anti-OX40 antibody or antigen-binding fragment thereof wherein the amino acid sequence of the heavy chain variable region and/or light chain variable region comprises one or more (preferably no more than 10, more preferably no more than 6, 5, 4, 3, 2 or 1) amino acid changes (preferably amino acid substitutions, more preferably amino acid conservative substitutions), compared with the heavy chain variable region and/or light chain variable region of the antibody specifically disclosed herein, and preferably, the amino acid changes do not occur in a CDR region.

In some embodiments, the anti-OX40 antibody or antigen-binding fragment thereof provided by the present invention comprises a heavy chain variable region (VH), wherein the VH comprises an amino acid sequence identical to or having at least 90%, 91%, 92%, 93%, 94%, 95%, 96%, 97%, 98% or 99% sequence identity to the amino acid sequence as set forth in SEQ ID NO: 1, 2, 3, 4 or 5.

In some embodiments, the anti-OX40 antibody or antigen-binding fragment thereof provided by the present invention comprises a light chain variable region (VL), wherein the VL comprises an amino acid sequence identical to or having at least 90%, 91%, 92%, 93%, 94%, 95%, 96%, 97%, 98% or 99% sequence identity to the amino acid sequence as set forth in SEQ ID NO: 6, 7, 8, 9 or 10.

In an embodiment of the present invention, the amino acid changes described herein include amino acid substitutions, insertions or deletions. Preferably, the amino acid changes described herein are amino acid substitutions, preferably conservative substitutions.

In a preferred embodiment, the amino acid changes of the present invention occur in regions outside CDRs (for example, in FRs). More preferably, the amino acid changes of the present invention occur in regions outside the heavy chain variable region and/or outside the light chain variable region. In some embodiments, the amino acid changes occur in a heavy chain constant region and/or a light chain constant region.

In some embodiments, the antibodies of the present invention comprising amino acid changes have comparable or similar properties to the specific antibodies disclosed herein.

In some embodiments, the anti-OX40 antibody of the present invention includes post-translational modifications to CDRs, light chain variable regions, heavy chain variable regions, light chains, or heavy chains.

In some embodiments, the anti-OX40 antibody provided by the present invention is a full-length antibody, a single-domain antibody such as a VHH, a Fab, a Fab', a Fab'-SH, a (Fab')2, a single-chain antibody such as a scFv, a Fv, a dAb (domain antibody) or a bis (multi) specific antibody.

In some embodiments, the anti-OX40 antibody provided by the present invention is an antibody in the form of any IgG isotype, such as an antibody in the form of IgG1, IgG2, IgG3 or IgG4.

In some embodiments, the present invention also provides antibodies with altered effector function(s). The term "effector functions" refer to those biological activities attributable to Fc region of an antibody, which vary with the antibody class. There are five major antibody classes: IgA, IgD, IgE, IgG, and IgM, and some of these can be further divided into subclasses (isotypes), for example, IgG1, IgG2, IgG3, IgG4, IgA1, and IgA2. The effector functions of antibodies include, for example, but are not limited to: C1q binding and complement dependent cytotoxicity (CDC); Fc receptor binding; antibody-dependent cell-mediated cytotoxicity (ADCC); phagocytosis; recruitment of immune cells; and antibody cross-linking mediated by the binding of a Fc region to a FcR receptor on a cell surface. As understood by those skilled in the art, a suitable antibody Fc region sequence can be selected according to needs, such as whether it is desired to recruit the immune system to kill target cells, or induce the cross-linking of the antibody by interacting with FcR. For example, when immune system recruitment and target cell killing are the desired properties of the antibody of interest, the Fc region of the antibody can be selected or further modified to provide enhanced binding to activated FcγR receptors and/or complement to promote, for example, ADCC or CDC effector functions. For another example, in the case where immune system recruitment is undesirable, the Fc region of the antibody can be selected or further modified to reduce the effector function. For example, the Fc region of human IgG2 or IgG4 subtype can be used, or the Fc region of IgG1 subtype with mutations such as N297A can be used. In addition, an Fc region can be selected or mutated so that the antibody containing it selectively binds to one or more Fc receptors, while the binding to another one or more FcRs is reduced or eliminated, so as to achieve the adjustment of antibody effector functions, such as enhancing the cross-linking of antibodies while changing the intensity of ADCC activity. See, for example, Xinhua Wang et al., IgG Fc engineering to modulate antibody effector functions, Protein Cell 2018, 9 (1): 63-73, DOI 10.1007/s13238-017-0473-8; Shields R L, High Resolution Mapping of the Binding Site on Human IgG1 for FcγRI, FcγRII, FcγRIII and FcRn and Design of IgG1 Variants with Improved Binding to the FcγR, 2001, J Biol Chem. 2001 Mar. 2; 276 (9): 6591-604. Epub 2000 Nov. 28.

The present invention provides antibody variants possessing some but not all effector functions that make the antibody variants desirable candidates for applications where the in vivo half-life of the antibody is important, and certain effector functions (such as complements and ADCC) are unnecessary or harmful. In vitro and/or in vivo cytotoxicity assays can be conducted to confirm the reduction/depletion of CDC and/or ADCC activities. For example, a Fc receptor (FcR) binding assay can be conducted to ensure that an antibody lacks FcγR binding (and therefore may lack ADCC activity or antibody cross-linking activity), but retains FcRn binding ability. NK cells, the main cells that mediate ADCC, only express Fc γ RIII, while monocytes express Fcγ RI, Fcγ RII and Fcγ RIII. FcR expression on hematopoietic cells is summarized in Table 3 on page 464 of Ravetch and Kinet, Annu. Rev. Immunol 9: 457-492 (1991). The binding sites with FcγRI, FcγRII, FcγRIII and FcRn on human IgG1 have been depicted, and variants with improved binding have been described (see Shields et al., J. Biol. Chem. 276: 6591-6604, 2001).

In some embodiments, one or more amino acid modifications can be introduced into the Fc region of the antibody provided by the present invention to produce Fc region variants. The Fc region variant can comprise a human Fc region sequence (such as the Fc region of human IgG1, IgG2, IgG3, or IgG4) comprising amino acid modifications (such as substitutions) at one or more amino acid positions. For example, a number of modifications to human IgG1 to enhance or reduce its binding to FcγR and enhance or reduce the corresponding function are summarized in article of Bruhns and Jönsson published in Immunol Rev. 2015 November; 268 (1): 25-51, page 44.

In some embodiments, the antibody provided by the present invention comprises a human IgG1 Fc region variant, which has an FcγR binding activity (such as antibody cross-linking activity) which is reduced or deficient. In some embodiments, the human IgG1 Fc region variant comprises one or more amino acid substitution, and in particular, the amino acid substitution selected from amino acid substitutions at positions E233, L234, L235, N297, and P331 of an immunoglobulin heavy chain. In some embodiments, the human IgG1 Fc region variant comprises one or more amino acid substitution selected from E233P, L234A, L235A, L235E, N297A, N297G, N297D and P331S. In some embodiments, the amino acid substitution of the human IgG1 Fc region variant is N297A.

In one aspect, the antibody provided herein is modified to increase or decrease the degree of glycosylation of the antibody. The addition or deletion of the glycosylation sites of an antibody can be conveniently achieved by changing the amino acid sequence so as to produce or remove one or more glycosylation sites. Glycosylation can be changed, for example, to increase affinity of the antibody for the "antigen". Such carbohydrate modification can be accomplished, for example, by changing one or more glycosylation sites within the antibody sequence. For example, one or more amino acid substitutions can be made, which results in the elimination of one or more variable region framework glycosylation sites, thereby eliminating glycosylation at this site. This aglycosylation can increase affinity of the antibody for the antigen. Such a method is described in, for example, U.S. Pat. No. 5,426,300. When the antibody comprises an Fc region, the saccharides attached to same can be changed. In some applications, modifications to remove undesired glycosylation sites are useful, such as removal of fucose modules to improve antibody-dependent cell-mediated cytotoxicity (ADCC) functions. In other applications, galactosylation modification can be made to modify complement-dependent cytotoxicity (CDC).

In some embodiments, it may be desirable to produce cysteine engineered antibody, e.g., "thioMAb", in which one or more residues of the antibody are substituted with cysteine residues.

In some embodiments, the antibody provided herein may be further modified to comprise additional non-protein moieties that are known in the art and readily available. A moiety suitable for antibody derivatization includes, but is not limited to, a water soluble polymer. Non-limiting examples of water soluble polymers include, but are not limited to, polyethylene glycol (PEG), ethylene glycol/propylene glycol co-polymers, carboxymethylcellulose, dextran, polyvinyl alcohol, polyvinyl pyrrolidone, poly-1,3-dialkane, poly-1,3,6-trialkane, ethylene/maleic anhydride co-polymer, polyaminoacids (either homopolymers or random copolymers), and dextran or poly(n-vinyl pyrrolidone)polyethylene glycol, propropylene glycol homopolymers, polypropylene oxide/ethylene oxide co-polymers, polyoxyethylated polyols (e.g., glycerol), polyvinyl alcohol, and mixtures thereof.

In some embodiments, the antibody of the present invention has one or more of the following properties:

(i) binding to human OX40, especially to the extracellular domain of human OX40, with a high affinity, such as with a $K_D$ value of less than 100 nM, such as less than 50 nM, such as less than 30 nM, preferably less than 10 nM or 5 nM, wherein preferably the $K_D$ value is measured using surface plasmon resonance assay;

(ii) binding to human OX40 expressed on the surface of cells (such as T cells), with a high affinity, such as with a EC50 value of less than 100 nM, such as less than 50 nM, such as less than 40 nM, preferably less than 20 nM, more preferably less than 10 nM or 5 nM, wherein preferably the EC50 value is measured using FACS assay;

(iii) blocking the binding of human OX40 to its ligand OX40L, with an inhibition rate of at least 50%, for example, at least 60%, 70%, 80%, 85% or 90%, for example, as determined by ELISA, and preferably with an IC50 value of less than 10 nM, more preferably less than 1 nM;

(iv) showing the same or similar binding affinity and/or specificity as any antibody listed in Table 2;

(v) inhibiting (for example, competitively inhibiting) the OX40 binding of any antibody listed in Table 2;

(vi) binding the same or an overlapping epitope as any antibody listed in Table 2;

(vii) having the same or similar biological activity as any antibody listed in Table 2.

In some embodiments, the OX40 antibody of the present invention is an agonist antibody, comprising an Fc region that binds to FcR (e.g., FcγR), such as a human IgG1, IgG2, or IgG4 Fc region or a variant thereof, preferably a human IgG1 or IgG2 Fc region or a variant thereof. The variant preferably has a binding affinity for FcγR comparable to or stronger than that of the parent Fc region (e.g., a native-sequence Fc region). Preferably, the antibody achieves cross-linking by binding its Fc region to FcγR expressed on the cell surface. Preferably, the antibody comprises a human IgG1 or IgG2 Fc region sequence identical to the Fc region sequence of the constant region sequence as set forth in SEQ ID NO: 21 or 22, or comprises a human IgG1 or IgG2 Fc region variant having at least 95%, 96%, 97% or 99% identity to the Fc region sequence of the constant region sequence as set forth in SEQ ID NO: 21 or 22, or having no more than 10, 5 or 1-3 amino acid changes relative to the Fc region sequence of the constant region sequence as set forth in SEQ ID NO: 21 or 22.

In some embodiments, the OX40 agonist antibody of the present invention has one or more of the following properties:

(i) binding to human OX40 with a high affinity, such as with a $K_D$ value of less than 10 nM, more preferably less than 5 nM, wherein preferably the $K_D$ value is measured using surface plasmon resonance assay;

(ii) binding to human OX40 expressed on the surface of cells (such as activated CD4+ T cells) with a high affinity, such as with a EC50 value of less than 10 nM, more preferably less than 5 nM, wherein preferably the EC50 value is measured using FACS assay;

(iii) activating OX40-mediated signal transduction activity;

(iv) having a T-cell agonistic activity, wherein the T-cell agonistic activity of the antibody can be evaluated, for example, by detecting cytokines such as IFNγ released by activated T cells in the presence of the antibody, and in some embodiments, the EC50 value of the antibody is less than 10 nM, preferably less than 5 nM;

(v) inhibiting tumor growth, such as inhibiting the growth of melanoma cells.

In some embodiments, the OX40 antibody of the present invention is an antagonist antibody. In some embodiments, the antibody comprises an Fc region variant, wherein, for example, relative to a parent Fc region (e.g., a native-sequence Fc region), the binding affinity of the Fc region variant for FCγR is reduced or substantially eliminated. In some embodiments, the antibody of the present invention substantially does not bind to FcγR expressed on a cell surface, and FcγR-mediated antibody cross-linking does not occur. In some embodiments, the antibody of the present invention comprising an Fc region variant has reduced or eliminated FcγR-mediated effector functions relative to the corresponding antibody comprising a parent Fc region (e.g., a native-sequence Fc region). Preferably, the Fc region of the antibody comprises a mutation selected from: E233P, L234A, L235A, L235E, N297A, N297G, N297D, P331S, or a combination thereof. More preferably, the Fc region of the antibody is a human IgG1 Fc region comprising the N297A mutation. In some embodiments, the antibody comprises a human IgG1 Fc region sequence identity to the Fc region sequence of the constant region sequence as set forth in SEQ ID NO: 21, or comprises a human IgG1 Fc region variant having at least 95%, 96%, 97%, 98% or 99% identity to the Fc region sequence of the constant region sequence as set forth in SEQ ID NO: 21, or having no more than 10, 5 or 1-3 amino acid changes relative to the Fc region sequence of the constant region sequence as set forth in SEQ ID NO: 21, and comprises a mutation(s) that reduces the binding affinity of the Fc region to FcγR, preferably N297 mutation, more preferably N297A.

In some embodiments, the OX40 antagonist antibody of the present invention has one or more of the following properties:

(i) binding to human OX40 with a high affinity, such as with a $K_D$ value of less than 10 nM, more preferably less than 5 nM, wherein preferably the $K_D$ value is measured using surface plasmon resonance assay;

(ii) binding to human OX40 expressed on the surface of cells (such as activated CD4+ T cells) with a high affinity, such as with a EC50 value of less than 10 nM, more preferably less than 5 nM, wherein preferably the EC50 value is measured using FACS assay;

(iii) blocking the binding of OX40 to its ligand OX40L, with an inhibition rate of at least 70%, preferably at least 80%, 85% or 90%, for example, as determined by ELISA, and preferably with an IC50 value of less than 10 nM, more preferably less than 1 nM;

(iv) blocking OX40-mediated signal transduction activity;

(v) having a T-cell antagonistic activity, wherein the T-cell antagonistic activity of the antibody can be evaluated, for example, by detecting cytokines such as IFNγ released by activated T cells in the presence of the antibody and ligand OX40L to assess the inhibition of OX40L-medicated T-cell activation by the antibody, and in some embodiments, the IC50 value of the antibody is less than 5 nM, preferably less than 1 nM;

(vi) exhibiting an anti-immune rejection activity, such as reducing immune rejection in graft-versus-host diseases.

Antibody Expression

The present invention relates to a host cell comprising one or more expression vectors and a method for producing any antibody or antigen-binding fragment thereof of the present invention, wherein the method comprises culturing the host cell, purifying and recovering the antibody or antigen-binding fragment.

In one aspect, the present invention provides a nucleic acid encoding any of the above anti-OX40 antibodies or antigen-binding fragments thereof. For example, the present invention provides a nucleic acid encoding a segment comprising a heavy chain, a light chain, a variable region or a complementarity determining region described herein. In some aspects, the nucleic acid encoding the heavy chain variable region has at least 85%, 89%, 90%, 91%, 92%, 93%, 94%, 95%, 96%, 97%, 98%, 99% or 100% sequence identity to the nucleic acid sequence as set forth in SEQ ID NO: 17 or 18. In some aspects, the nucleic acid encoding the light chain variable region has at least 85%, 89%, 90%, 91%, 92%, 93%, 94%, 95%, 96%, 97%, 98%, 99% or 100% sequence identity to the nucleic acid sequence as set forth in SEQ ID NO: 19 or 20.

In one aspect, one or more vectors comprising the nucleic acid are provided. In some embodiments, the vector is an expression vector. The choice of an expression vector depends on the host cell in which the vector is intended to be expressed. Generally, an expression vector comprises a promoter and other regulatory sequence (e.g., enhancer) operably linked to a nucleic acid encoding an anti-OX40 antibody or antigen-binding fragment thereof. In some embodiments, the expression vector further comprises a sequence encoding the antibody constant region.

In one aspect, the present invention provides host cells for expressing the recombinant antibodies of the present invention, including prokaryotic or eukaryotic cells. In some embodiments, *Escherichia coli* is a prokaryotic host that can be used to clone and express the nucleic acid of the present invention. Other suitable microbial hosts include bacilli, such as *Bacillus subtilis*, and other Enterobacteriaceae, such as *Salmonella, Serratia*, and various *Pseudomonas*. In these prokaryotic hosts, expression vectors can also be prepared, which generally comprise expression control sequences (for example, an origin of replication) that are compatible with the host cells. In some embodiments, mammalian host cells are used to express and produce the anti-OX40 antibody polypeptides of the present invention. For example, they may be hybridoma cell lines expressing endogenous immunoglobulin genes, or mammalian cell lines with exogenous expression vectors, including normal human cells, or immortalized animal or human cells. For example, many suitable host cell lines capable of secreting intact immunoglobulin have been developed, including CHO cell lines, various COS cell lines, HEK293 cells, myeloma cell lines, transformed B cells and hybridomas.

In one aspect, the present invention provides a method for preparing an anti-OX40 antibody, wherein the method comprises introducing an expression vector into a mammalian host cell, and allowing the antibody to be expressed in the host cell by culturing the host cell for a sufficient period of time, or more preferably, secreting the antibody into the medium in which the host cell is grown to produce the antibody. Standard protein purification methods can be used to recover antibodies from the culture medium. The antibody molecule prepared as described herein can be purified by known available techniques such as high performance liquid chromatography, ion exchange chromatography, gel electrophoresis, affinity chromatography, size exclusion chromatography, etc. The actual conditions used to purify a specific protein also depend on factors such as net charge, hydrophobicity, and hydrophilicity, which are obvious to a person skilled in the art. The purity of the antibody molecule of the present invention can be determined by any of a variety of well-known analytical methods, including size exclusion chromatography, gel electrophoresis, high performance liquid chromatography, etc.

Antibodies expressed by different cell lines or expressed in transgenic animals are likely to have different glycosylation types from each other. However, all antibodies encoding by the nucleic acids provided herein or comprising the amino acid sequences provided herein are parts of the present invention, regardless of the glycosylation types of the antibodies.

Assays

The physical/chemical properties and/or biological activities of the anti-OX40 antibody provided herein can be identified, screened, or characterized by a variety of assays known in the art. In one aspect, the antigen-binding activity of the antibody of the present invention is tested, for example, by a known method such as ELISA and Western blot. Methods known in the art can be used to determine binding to OX40, and exemplary methods are disclosed herein.

The present invention also provides an assay method for identifying anti-OX40 antibodies with a desired biological activity. The biological activities can include, for example, binding to OX40 (for example, binding to human OX40), increasing OX40-mediated signal transduction (e.g., increasing NFκB-mediated transcription), enhancing T effector cell function (e.g., by increasing effector T cell proliferation and/or increasing cytokine production (e.g., gamma interferon) by effector T cells), etc. Antibodies having such biological activities in vivo and/or in vitro are also provided.

In certain embodiments, the antibodies of the present invention are tested for such biological activities.

Cells for use in any of the above-mentioned in vitro assay methods include cell lines that naturally express OX40 or are engineered to express OX40, such as tumor cell lines. Such cells also include cell lines that normally do not express OX40 and which which are transfected with DNA encoding the OX40 to express OX40.

It is understood that the immunoconjugates or immune fusions of the present invention can be used, in place of or in addition to the anti-OX40 antibody, to perform any of the above-mentioned assay methods.

It is understood that a combination of an anti-OX40 antibody and another active agent can be used to perform any of the above-mentioned assay methods.

Immunoconjugate and Immune Fusion

In some embodiments, the present invention provides an immunoconjugate, comprising any anti-OX40 antibody or antigen-binding fragment thereof provided by the present invention and another substance. In one embodiment, the another substance is, for example, a cytotoxic agent.

In some embodiments, the present invention provides an immune fusion comprising any anti-OX40 antibody or antigen-binding fragment thereof.

In some embodiments, the immunoconjugate and the immune fusion are used for preventing or treating OX40-related diseases or conditions.

Pharmaceutical Composition

The pharmaceutical composition of the present invention may include the antibody of the present invention and a pharmaceutically acceptable auxiliary substance. In some other embodiments, the pharmaceutical composition of the present invention can be included in a pharmaceutical kit. In some other embodiments, the pharmaceutical composition of the present invention can be included in a kit, such as a diagnostic kit.

As used herein, a "pharmaceutical carrier" includes any and all solvents, dispersion medium, isotonic agents, absorption delaying agents, etc., that are physiologically compatible. Pharmaceutical carriers suitable for the present invention can be sterile liquids, such as water and oils, including those of petroleum, animal, vegetable or synthetic origin, such as peanut oil, soybean oil, mineral oil, sesame oil, etc. Water is a preferred carrier when the pharmaceutical composition is administered intravenously. It is also possible to use saline solutions, aqueous dextrose and glycerol solutions as liquid carriers, particularly for injectable solutions.

Suitable pharmaceutical excipients include starch, glucose, lactose, sucrose, gelatin, malt, rice, flour, chalk, silica gel, sodium stearate, glycerol monostearate, talc, sodium chloride, dry skim milk, glycerol, propylene, diol, water, ethanol, etc. For the application of excipients and uses thereof, see also "Handbook of Pharmaceutical Excipients", fifth edition, R. C. Rowe, P. J. Seskey and S. C. Owen, Pharmaceutical Press, London, Chicago. The composition may also contain a small amount of a wetting agent or an emulsifier, or a pH buffering agent. These compositions can be in the form of solutions, suspensions, emulsions, tablets, pills, capsules, powders, sustained release agents, etc. Oral formulation can comprise standard carriers such as pharmaceutical grades of mannitol, lactose, starch, magnesium stearate, saccharin, etc.

The present invention provides a pharmaceutical composition comprising one or more monoclonal antibodies binding to OX40 or antigen-binding fragments thereof, or nucleic acids, vectors or host cells, or immunoconjugates or immune fusions. It should be understood that the anti-OX40 antibody provided by the present invention, or antigen-binding fragment thereof, the nucleic acid, the vector or the host cell thereof, or the immunoconjugate, or the immune fusion in a pharmaceutical composition can be formulated with suitable pharmaceutical carriers, excipients and another co-administrated agent suitable used in a pharmaceutical preparation, so as to provide improved transfer, delivery, tolerance, etc.

The pharmaceutical preparation comprising the anti-OX40 antibody described herein can be prepared by mixing the anti-OX40 antibody or antigen-binding fragment thereof of the present invention having the desired degree of purity with one or more optional pharmaceutically acceptable excipients, preferably in the form of aqueous solutions or lyophilized preparations. Exemplary lyophilized antibody preparations are described in U.S. Pat. No. 6,267,958. Aqueous antibody preparations include those described in U.S. Pat. No. 6,171,586 and WO 2006/044908, the latter describing a preparation comprising a histidine-acetate buffering agent.

The pharmaceutical compositions or preparations of the present invention may also comprise one or more other active ingredients that are required for the treatment of specific diseases, preferably those active ingredients with complementary activities that do not adversely affect each other. For example, it is desirable that other therapeutic agents are also included. In some embodiments, the other therapeutic agents are chemotherapeutic agents, radio therapeutic agents, cytokines, vaccines, other antibodies, immunomodulators or other biomacromolecular drugs.

In some embodiments, the pharmaceutical composition of the present invention may also comprise a nucleic acid encoding the anti-OX40 antibody or an antigen-binding fragment thereof.

Methods and Uses

The present invention provides a method for preventing, diagnosing or treating OX40-related diseases or conditions. The method comprises administering to a patient in need thereof an effective amount of the anti-OX40 antibody, or an antigen-binding fragment thereof, or an immunoconjugate or an immune fusion or a pharmaceutical composition comprising same, or a nucleic acid, a vector or a host cell described herein.

In one aspect, the present invention provides the use of an anti-OX40 antibody or antigen-binding fragment thereof, or an immunoconjugate or an immune fusion or a pharmaceutical composition comprising same, in the manufacture or preparation of drugs for the prevention or treatment of OX40-related diseases or conditions in subjects.

In one aspect, the anti-OX40 antibodies provided by the present invention, and antigen-binding fragments thereof, and a pharmaceutical composition comprising same can be used as a therapeutic agent to prevent or treat OX40-related diseases or conditions in a subject. For OX40-related diseases in subjects identified by using standard methods, the anti-OX40 antibodies and antigen-binding fragments thereof disclosed in the present invention, and pharmaceutical compositions or immunoconjugates or immune fusions comprising same, or the nucleic acids, vectors or host cells described herein can be administered.

In some embodiments, the methods and uses described herein further comprise administering to the individual an effective amount of at least one additional therapeutic agent or procedure. In some embodiments, the therapeutic agents are, for example, chemotherapeutic agents, radio therapeutic agents, cytokines, vaccines, other antibodies, immunomodulators or other biomacromolecular drugs. In some embodiments, the therapeutic procedures include surgery; and radiation therapy, local irradiation or focus irradiation, etc.

The above-mentioned combination therapy includes combined administration (in which two or more therapeutic agents are contained in the same or separate preparations) and separate administration, wherein the administration of the anti-OX40 antibody or antigen-binding fragment thereof of the present invention may occur prior to, simultaneously with, or after administration of additional therapeutic agent and/or adjuvant and/or procedure.

In some embodiments, the OX40-related diseases or conditions of the present invention refer to diseases or conditions related to abnormal OX40 expression, activity and/or signal transduction in a subject, including but not limited to cancers, inflammation and autoimmune diseases. In some embodiments, in OX40-related diseases or conditions, the nucleic acid (level or content) encoding OX40 is increased, or OX40 expression is increased, or protein level or activity of OX40 is increased, or signal transduction mediated by OX40 is increased. In some other embodiments, in OX40-related diseases or conditions, the nucleic acid (level or content) encoding OX40 is reduced, or OX40 expression is decreased, or protein level or activity of OX40 is decreased, or signal transduction mediated by OX40 is decreased.

In some embodiments, the treatment of the diseases or conditions will benefit from inhibiting OX40 at the nucleic acid or protein level, or from blocking the binding of OX40 to its ligand or inhibiting OX40-mediated signal transduction.

In some other embodiments, the treatment of the diseases or conditions will benefit from increasing OX40 at the nucleic acid or protein level, or benefit from enhancing OX40-mediated signal transduction.

In some embodiments, OX40-related diseases or conditions are cancers. In particular, the cancers include, but are not limited to, solid tumors, breast cancer, urothelial cancer, melanoma, kidney cancer, ovarian cancer, head and neck cancer, stomach cancer, liver cancer, small-cell lung cancer, non-small cell lung cancer, skin cancer, mesothelioma, lymphoma, leukemia, myeloma, prostate cancer, lymphatic leukemia and sarcoma. Preferably, the antibody for preventing, diagnosing or treating OX40-related cancers is an OX40 agonist.

In some embodiments, OX40-related diseases or conditions are inflammation and/or autoimmune diseases. In some embodiments, OX40-related inflammation and/or autoimmune diseases are selected from idiopathic dermatitis, rheumatoid arthritis, asthma (e.g., allergic asthma), COPD, autoimmune uveitis, multiple sclerosis, lupus (such as systemic lupus erythematosus), ulcerative colitis, scleroderma, and graft-versus-host disease (GVHD). Preferably, the antibody for treating or preventing OX40-related inflammation and/or autoimmune diseases is an OX40 antagonist.

In some embodiments, the subject may be a mammal, e.g., a primate, preferably a higher primate, e.g., a human (e.g., an individual suffering from a disease described herein or having a risk of suffering from a disease described herein). In one embodiment, the subject suffers from or has a risk of suffering from a disease described herein (e.g., cancer). In certain embodiments, the subject receives or has received other treatments, such as chemotherapy and/or radiation therapy.

The antibody or antigen-binding fragment of the present invention may be administered in any suitable manner, including oral, parenteral, intrapulmonary and intranasal administration, and, if topical treatment is needed, it can be administered intralesionally. Parenteral infusion includes intramuscular, intravenous, intraarterial, intraperitoneal or subcutaneous administration. Administration can be carried out by any suitable route, for example by injection, such as intravenous or subcutaneous injection, depending in part on whether the administration is short-lived or long-term. Various administration regimens are contemplated herein, including but not limited to single or multiple administrations at various time points, bolus administration, and pulse infusion.

The antibody or antigen-binding fragment of the present invention will be formulated and administered in a manner consistent with good medical practice. The factors considered in this case include the specific disease being treated, the specific mammal being treated, the clinical condition of an individual patient, the cause of a disease, the delivery site of a drug, the administration mode, the dosing schedule, and other factors known to practitioners. Optionally, the antibody is formulated with one or more agents currently used to prevent or treat the disease. The effective amount of these other agents depends on the amount of antibody present in the preparation, the condition to be treated, or the therapeutic mode, and other factors discussed above.

In order to prevent or treat diseases, the antibody or antigen-binding fragment of the present invention (when used alone or in combination with one or more additional therapeutic agents) will be administrated in a suitable dosage depending on the type of diseases to be treated, the type of antibodies, the severity and course of the disease, whether the antibody is for the purpose of prevention or treatment, the previous treatment, the patient's clinical history and response to the antibody and the judgment of the attending physician. The antibody is appropriately administered to the patient at one time or over a series of treatments.

In certain embodiments, any anti-OX40 antibody or antigen-binding fragment thereof provided herein can be used to detect the presence of OX40 in a biological sample. The term "detection" when used herein includes quantitative or qualitative detection. In certain embodiments, the biological sample is blood, serum, or other liquid samples of biological origin. In certain embodiments, the biological sample comprises cells or tissues. In some embodiments, the biological sample is from hyperproliferative or cancerous lesion related lesions.

In one embodiment, the antibody or antigen-binding fragment thereof of the present invention can be used to diagnose OX40-related diseases or conditions, such as cancers, for example to evaluate (e.g., monitor) the treatment or progression of the diseases described herein, and diagnosis and/or staging thereof in an individual. In certain embodiments, a labeled anti-OX40 antibody or antigen-binding fragment thereof is provided. Labels include, but are not limited to, labels or moieties that are directly detectable (such as fluorescent labels, chromophore labels, electron-dense labels, chemiluminescent labels, and radioactive labels), and moieties that are indirectly detectable, such as enzymes or ligands, for example, by enzymatic reactions or intermolecular interactions. In some embodiments, provided herein is a kit for diagnosing OX40-related diseases, which kit comprises the antibody or antigen-binding fragment thereof of the present invention.

In some embodiments provided herein, the sample is obtained prior to treatment with the anti-OX40 antibody or antigen-binding fragment thereof. In some embodiments, the sample is obtained prior to treatment with other therapies. In some embodiments, the sample is obtained during or after treatment with other therapies.

The present invention includes any combinations of specific embodiments described herein. It should be understood that although the specific content and examples are described to illustrate the preferred embodiments of the present invention, these are merely illustrative and used as examples. The present invention further covers embodiments modified on the basis of the preferred embodiments of the present invention that are obvious to a person skilled in the art. For all purposes, all publications, patents and patent applications cited herein, including citations, will be incorporated herein by reference in their entirety.

EXAMPLES

Example 1 Preparation and Screening of Hybridoma-Derived Antibodies

The OX40 antibodies were obtained by hybridoma technique. The recombinant OX40-Fc protein (R & D, Cat 3388-OX) containing the human OX40 extracellular domain with an Fc tag was used as antigen to immunize mice. In short, C57BL/6 and BALB/c mice were immunized with OX40-Fc mixed and emulsified with complete or incomplete Freund's adjuvant (Sigma-Aldrich). The mice were subjected to one round of immunization (complete Freund's adjuvant) and two rounds of booster immunization (incomplete Freund's adjuvant), and blood was collected after each booster immunization. The binding activity of the serum collected from the mice after each round of boost was detected by ELISA with the recombinant human OX40-His protein (R & D Systems, Cat 9969-OX), and the binding activity of the serum to CHO cells (constructed by GenScript) overexpressing human OX40 was detected by flow cytometry (FACS). The mice with a high serum titer were selected for fusion. 4 days before fusion, the recombinant OX40-Fc protein was intraperitoneally injected into mice for final booster immunization. On the day of fusion, mice were euthanized, and then spleen was taken from the mice and homogenized to obtain single cell suspension. The mouse spleen cells were fused with mouse myeloma cell line SP2/0 cells (purchased from ATCC) by means of an electrofusion apparatus. The fused cells were resuspended in a medium containing HAT (hypoxanthine, aminopterin and thymidine deoxynucleotide, GIBCO, Cat 21060017), inoculated into a 96-well plate and cultured at 37° C. for 7 days. The antibodies secreted by the hybridoma cells in the supernatant were identified by OX40-related functional assays (such as binding specificity to human OX40 and activity in activation of T cells). The positive hybridoma clones were subcloned for single or multiple rounds to obtain a monoclone. After screening, 38E11 was finally chosen as an optimal hybridoma clone (the antibody secreted thereby being referred to as 38E11).

The candidate hybridoma cells 38E11 was subjected to an expanded culture, and after 7 to 10 days of culturing, the supernatant was collected, centrifuged and filtered to remove cells and debris. The supernatant was passed through a protein A purification column (Genscript), then the column was washed and equilibrated with a buffer containing 0.05 M Tris and 1.5 M NaCl (pH 8.0), and then eluted with 0.1 M sodium citrate (pH 3.5); and the eluent was immediately neutralized with one ninth volume of 1 M Tris-HCl (pH 9), and then dialyzed into PBS buffer. Finally, the hybridoma-derived antibody 38E11 was obtained for further characterization.

1.1 Detection of Binding Activities of Antibodies to OX40 Extracellular Domain Protein by ELISA The recombinant human OX40-His (R & D, Cat 9969-OX) was coated onto 96-well plates. After blocking, serially diluted mouse serum or antibodies were added and incubated. After washing plates with PBS containing 0.5% Tween20, HRP-labeled anti-mouse IgG secondary antibody was added for incubation, and the plates were developed with TMD, and the OD450 value was read via a microplate reader.

As shown in Table 1, the finally obtained hybridoma-derived antibody 38E11 has a high binding activity to human OX40 protein, with an $EC_{50}$ of 0.276 nM.

1.2 Detection of Binding Activities of Antibodies to OX40 on Activated T Cells by FACS Primary human PBMC were isolated from whole blood obtained from healthy donors through density gradient centrifugation with Ficoll-Paque PLUS (GE Healthcare, Cat 17-1440-02). After centrifuge, the cells in the middle layer were collected and washed 3 times with PBS to obtain PBMC. Then, human T cells were isolated with Pan T Cell Isolation Kit (Miltenyi biotec, Cat 130-096-535) by magnetic beads isolation method according to the protocol recommended by the instructions. T cells were resuspended in RPMI 1640 (containing 10% FBS and penicillin/streptomycin bi-antibiotics) medium, and PHA-L and IL-2 (or Con-A and hIL-2) were added for 2-day stimulation to induce the expression of OX40 from the T cells. The activated T cells were washed once with PBS containing 2% FBS, the serially diluted OX40 antibodies were added, and incubated at 4° C. for 30 minutes. The cells were washed twice with PBS containing 2% FBS, PE-labeled anti-human IgG secondary antibody (Biolegend, Cat 409304) (or PE-labeled anti-mouse IgG secondary antibody (Biolegend, Cat 405307)) and APC-CY7 labeled antibody human CD4 antibody (Biolegend, Cat 300518) were added. The binding of OX40 antibody on the surface of CD4 positive T cells was detected by BD CantoII flow cytometry. A curve was fitted according to the median fluorescence intensity value, and $EC_{50}$ was calculated.

As shown in Table 1, the hybridoma-derived antibody 38E11 has binding activity to OX40 on human activated T cells, with an $EC_{50}$ of 0.8 nM.

1.3 Determination of T-Cell Agonistic Activities of Antibodies

The T-cell agonistic activity of the antibody is evaluated by detecting cytokine IFNγ released by activated T cells. In short, primary human PBMCs were isolated from whole blood obtained from healthy donors by density gradient centrifugation with Ficoll-Paque PLUS (GE Healthcare, Cat 17-1440-02). After centrifuge, the cells in the middle layer were collected and washed 3 times with PBS to obtain PBMC. Then, human T cells were isolated with Pan T Cell Isolation Kit (Miltenyi biotec, Cat 130-096-535) by magnetic beads isolation method according to the protocol recommended by the instructions. T cells were resuspended in RPMI 1640 (containing 10% FBS and penicillin/streptomycin bi-antibiotics) medium. After mixing anti-CD3 antibody (eBioscience, Cat 16-0037-85) and the serially diluted OX40 antibodies, the mixture was added to a 96-well plate at 100 μl/well, and the plate was coated at 37° C. for 2 h. Unbound antibodies were removed by washing with PBS, and isolated T cells were added to the wells. Supernatants were collected after 3 days of culture, and the concentrations of IFNγ in the supernatants were detected by ELISA (R & D, Ct SIF50) according to the standard detection method recommended by the instructions.

As shown in Table 1, the hybridoma-derived antibody 38E11 promoted IFNγ secretion by T cells, with an $EC_{50}$ value of 1.4 nM.

Table 1 also shows the functional activities of the reference anti-OX40 antibodies 11D4 and OX40mAb24 obtained by transient expression.

2.2 Humanized Design of Hybridoma-Derived Antibody

For antibody humanization, firstly, a human germline immunoglobulin gene highly homologous to the sequence of the variable region of murine antibody was searched in PDB Antibody database. The heavy chain variable region and light chain variable region of 38E11 have higher sequence homologies with human germline IGHV1-46*01 and human germline IGKV4-1*01, respectively. Then the amino acid sequences of the CDRs of the variable regions and the accurate boundary thereof are defined by the Kabat numbering system. In principle, human IGVH and IGVk with high homology with variable regions of a murine antibody are selected as templates and CDR grafting is used for humanization.

In order to maintain the activity in humanized antibody, generally, the amino acid sequences of the variable regions and the surrounding framework regions are also analyzed by using computer simulation technology and molecular docking, and their spatial 3-D binging modes are investigated. By calculating electrostatic force, van der Waals force, hydrophilicity and hydrophobicity, and entropy, the key residues in individual candidate antibody sequences are analyzed that may interact with OX40 or maintain the spatial structure, and be grafted back onto the selected human antibody gene framework. On this basis, the amino acid positions in the framework region that must be reserved are marked, and then the humanized antibody is synthesized. 7 sites in the heavy chain variable region of 38E11 antibody were selected for back mutations: V20L, M48I, R67K, M70L, R72V, V79A and T91S. According to the number and arrangement of the back mutations, four different humanized heavy chains VH1 (SEQ. ID No.: 2), VH2 (SEQ. ID No.: 3), VH3 (SEQ. ID No.: 4), and VH4 (SEQ. ID No.: 5) were designed respectively. 3 sites in the light chain variable region of 38E11 antibody were selected for back mutations: M4L,

TABLE 1

Functional activity of hybridoma-derived antibody 38E11

| Clone number ID | Binding to human OX40 protein (ELISA, EC50, nM) | Binding to OX40 on the surface of activated human T cells (FACS) ($EC_{50}$, nM) | Enhancement of IFNγ production by activated human T cells (ELISA) $EC_{50}$, nM) | Ratio of IFNγ maximum effect to background (in fold) |
|---|---|---|---|---|
| 11D4 | — | 0.4 | 8.0 | 5.6 |
| OX40mAb24 | — | 1.3 | 14.7 | 9.4 |
| 38E11 | 0.276 | 0.8 | 1.4 | 7.6 |

* Background: Control without anti-OX40 antibody

Example 2 Humanization of Hybridoma-Derived Antibody

2.1 Determination of Variable Region Sequences of Hybridoma-Derived Antibody Using the method for hybridoma sequencing, the cells of hybridoma clone 38E11 were subjected to an expanded culture; total RNA was extracted with TRIzol (purchased from Ambio) and reverse transcribed into DNA with antibody-specific primers (Takara, PrimerScript 1$^{st}$ Strand cDNA Synthesis Kit); and a gene fragment encoding mouse immunoglobulin V-region was amplified with antibody-specific primers and cloned. The variable region sequences were obtained by sequencing analysis, wherein the nucleotide sequence of the heavy chain variable region of 38E11 is as set forth in SEQ. ID No.: 17, and the nucleotide sequence of the light chain variable region of 38E11 is as set forth in SEQ. ID No.: 18.

V62I and L82V, and four different humanized light chains VL1 (SEQ. ID No.: 7), VL2 (SEQ. ID No.: 8), VL3 (SEQ. ID No.: 9), and VL4 (SEQ. ID No.: 10) were designed respectively. Thus, humanized 38E11 antibody Hu38E11 and its variants Hu38E11-v1, Hu38E11-v2, Hu38E11-v3 and Hu38E11-v4 were designed and further characterized. The amino acid sequences comprised in each antibody are shown in Tables 2 and 3.

2.3 Expression of Humanized Antibodies

The variable regions derived from the hybridoma-derived antibody 38E11, or the humanized sequences thereof were amplified and cloned into a vector comprising human IgG constant region to obtain an expressed plasmid. The heavy chain constant regions of those antibodies can be derived from any subtype of human IgG (such as, the amino acid sequences of the heavy chain constant regions of human IgG1 is as set forth in SEQ. ID No.:21, and the amino acid sequences of the heavy chain constant regions of human IgG2 is as set forth in SEQ. ID No.:22) or its variants. However, unless specifically indicated, the heavy chain constant regions of Hu38E11 and its variants were identical to the sequence of the heavy chain constant region of human IgG1. 293 cells were co-transfected with expression vectors comprising heavy and light chains. After culturing at 37° C. for 4-6 days, the supernatants were collected, and according to the above-described method, the recombinant antibodies were obtained by protein A affinity purification for further characterization of the antibodies.

TABLE 2

Amino acid sequences comprised in anti-OX40 antibodies

| 38E11 and variants thereof | VH amino acid sequence | VL amino acid sequence |
| --- | --- | --- |
| 38E11 | SEQ. ID No.: 1 | SEQ. ID No.: 6 |
| Hu38E11 | SEQ. ID No.: 2 | SEQ. ID No.: 7 |
| Hu38E11-v1 | SEQ. ID No.: 3 | SEQ. ID No.: 9 |
| Hu38E11-v2 | SEQ. ID No.: 4 | SEQ. ID No.: 7 |
| Hu38E11-v3 | SEQ. ID No.: 2 | SEQ. ID No.: 9 |
| Hu38E11-v4 | SEQ. ID No.: 4 | SEQ. ID No.: 8 |

TABLE 3

CDR amino acid sequences comprised in anti-OX40 antibodies (Rabat definition)

| CDR | Amino acid sequences |
| --- | --- |
| HCDR1 | SEQ. ID No.: 11 |
| HCDR2 | SEQ. ID No.: 12 |
| HCDR3 | SEQ. ID No.: 13 |
| LCDR1 | SEQ. ID No.: 14 |
| LCDR2 | SEQ. ID No.: 15 |
| LCDR3 | SEQ. ID No.: 16 |

Example 3 Detection of Binding Activities of Humanized Antibodies to OX40 on Activated T Cells by FACS According to the detection method described in the preceding Example 1.2, FACS was used to analyze the binding activities of humanized antibodies to OX40 on activated human T cells.

Results: As shown in Table 4, the humanized antibody Hu38E11 and its variants showed a superior binding activity to OX40 on the surface of activated human T cells.

TABLE 4

Binding activities of antibody Hu38E11 and its variants to OX40 on activated T cells

| Antibody | $EC_{50}$, nM |
| --- | --- |
| OX40mAb24 | 6.23 |
| Hu38E11 | 4.56 |
| Hu38E11-v1 | 5.03 |
| Hu38E11-v2 | 3.35 |
| Hu38E11-v3 | 3.48 |
| Hu38E11-v4 | 3.02 |

Example 4 Determination of T-Cell Agonistic Activities of Humanized Antibodies

According to the method described in the preceding Example 1.3, the agonistic activity of the humanized antibody on T cells was evaluated by detecting inflammatory cytokine IFNγ released by activated T cells in the presence of the antibody.

As shown in Table 5, the humanized antibody Hu38E11 and its variants can effectively promote activated T cells to release IFNγ, i.e., the humanized antibody Hu38E11 and its variants have T-cell agonistic activity. Compared with reference antibody OX40mAb24, the humanized antibody Hu38E11 and its variants showed a lower $EC_{50}$ value (a measure for activity in promoting T cells to release IFNγ), indicating a more significant agonistic activity.

TABLE 5

Agonistic activity of antibody Hu38E11 and its variants on T cells

| Antibody | $EC_{50}$ (nM) (maximum IFNγ concentration (ng/ml)) |
| --- | --- |
| OX40mAb24 | 7.1 (27370) |
| Hu38E11 | 2.4 (24821) |
| Hu38E11-v1 | 0.7 (21649) |
| Hu38E11-v2 | 1 (22517) |
| Hu38E11-v3 | 1.7 (22480) |
| Hu38E11-v4 | 0.9 (21720) |

Example 5 Detection of Binding Activities of Humanized Antibodies to Human OX40 by Biacore Biacore is used to determine the binding kinetic parameters by measuring surface plasmon resonance (SPR). This technology was used to detect the microscopic rate constants of the binding ($k_a$) and dissociation ($k_d$) of an antibody and an antigen. Based on the $k_a$ and the $k_d$ values, the affinity value of the antibody to the antigen is obtained. Both Biacore instrument and reagents were purchased from GE Healthcare. In particular, anti-human Fc antibody was immobilized on a CM5 sensor chip. The supernatants containing expressed antibody or the purified antibodies were diluted in a mobile phase buffer (10 mM HEPES, 150 mM NaCl, 3 mM EDTA, 0.05% Tween-20, pH 7.4), and flowed through the CM5 chip coated with anti-human Fc antibody. Then the serially diluted human OX40-His fusion proteins flowed through the detection chip to measure the binding of the antigen to the antibody, and then the mobile phase buffer flowed through the chip to detect the dissociation of the antigen from the antibody. The binding and dissociation signal data of the antigen and the antibody were collected at different concentrations, and fitted to the 1:1 Langmuir model to calculate the affinity between the antigen and the antibody.

As shown in Table 6, Hu38E11 binds to human OX40 with a high affinity, with a $K_D$ value of 2.36E-09 (M).

TABLE 6

Detection of kinetic constants of humanized antibodies binding to human OX40 by Biacore

| Antibody | $k_a$ (1/Ms) | $k_d$ (1/s) | KD (M) |
| --- | --- | --- | --- |
| OX40mAb24 | 2.95E+05 | 3.52E−03 | 1.19E−08 |
| 11D4 | 1.73E+05 | 4.35E−04 | 2.51E−09 |
| Hu38E11 | 1.67E+05 | 3.94E−04 | 2.36E−09 |

Example 6 Agonistic Activities of Humanized Antibody Hu38E11 on T Cells

According to the method described in the preceding Example 1.3, the agonistic activity of Hu38E11 (IgG2) with an antibody subtype of IgG2 on T cells was evaluated by detecting inflammatory cytokine IFNγ released by T cells.

Results: As shown in FIG. 1, under the condition that the plate was coated with the antibody, Hu38E11 (IgG2) also showed T-cell agonistic activity, with an $EC_{50}$ of 1.6 nM, which was lower than the reference antibody 11D4 ($EC_{50}$=5.3 nM).

Example 7 Blocking Effect of Humanized Antibodies on Binding of OX40 to OX40L

In this experiment, ELISA method was used to determine the activity of antibody Hu38E11 in blocking the binding of OX40 to its ligand OX40L. In short, OX40 (R & D systems, Cat 3388-OX) was diluted with PBS, then added to a 96-well plate, and the plate was coated overnight at 4° C. The plate was washed 3 times with PBS containing 0.5% Tween-20 to remove unbound proteins, then the plates were blocked by adding PBS containing 1% BSA at 200 μl/well, at room temperature for 1 h. After washing the plate 3 times with PBS containing 0.5% Tween-20, the serially diluted anti-OX40 antibodies were added to the 96-well plate at 100 μl/well, and incubated for 1 h at room temperature. The plate was washed 3 times with PBS containing 0.5% Tween-20. Then OX40L (R & D systems, Cat 1054-OX) at a final concentration of 50 ng/ml was added, and incubated at room temperature for 1 h. After washing the plate 3 times, a biotin-labeled anti-OX40L antibody (R & D systems, Cat BAF1054) was added, and incubated at room temperature for 1 h, then the plate was washed, and then HRP-labeled streptavidin (R & D systems, Cat DY998) was added and incubated at room temperature for 1 h. The plate was washed. 200 μl TMB color developing solution was added to each well for color development, and the reaction was stopped with 2N $H_2SO_4$. On a microplate reader, the O.D. value was detected at 450 nm, and the background O.D. value was measured at 570 nm.

Figure 2:
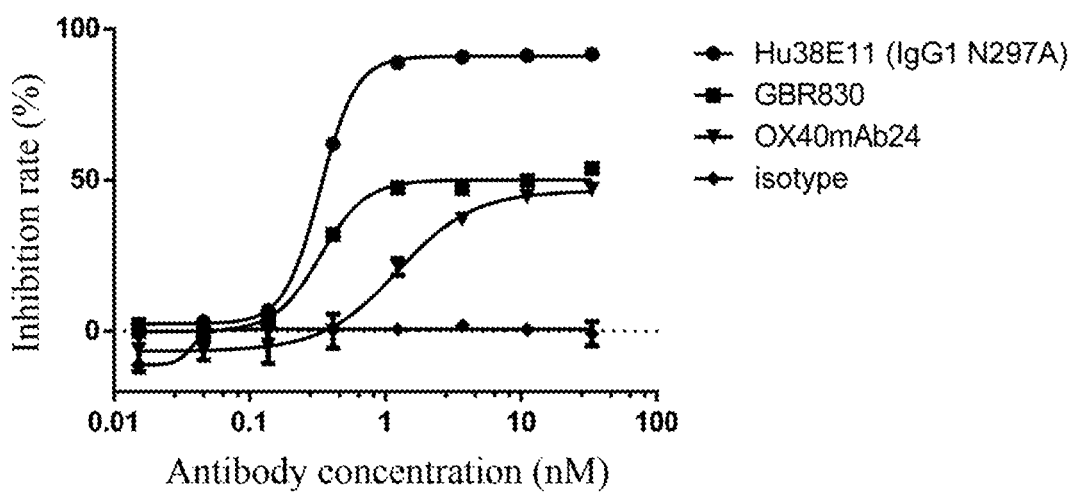
FIG. 2 shows the ability of antibody Hu38E11 (IgG1 N297A) to block the binding of OX40 to OX40L, as detected by ELISA.

As shown in FIG. 2, Hu38E11 (IgG1 N297A) blocked the binding of OX40 to OX40L, with a maximum inhibition rate of 90%, which was higher than the maximum inhibition rate of 50% of the reference antibodies GBR830 and OX40mAb24. The $IC_{50}$ values of Hu38E11 (IgG1 N297A) and GBR830 were around 0.3 nM, and the $IC_{50}$ value of OX40mAb24 was about 1.2 nM.

Example 8 Blocking Effects of Humanized Antibodies on OX40-OX40L-Mediated T Cell Activation Primary human PBMC were isolated from whole blood of health donor by density gradient centrifugation with Ficoll-Paque PLUS (GE Healthcare, Cat 17-1440-02). The middle layer was collected and washed 3 times with PBS to obtain PBMC. Then, primary human T cells were isolated by Pan T Cell Isolation Kit (Miltenyi Biotec, Cat 130-096-535) using magnetic beads according to the method recommended by the instructions. T cells were resuspended in RPMI 1640 (containing 10% FBS and penicillin/streptomycin bi-antibiotics) medium. The anti-CD3 antibody OKT3 (eBioscience, Cat 16-0037-85) was added to a 96-well plate at 100 ul/well, and coated at 37° C. for 2 h. Unbound antibodies were removed by washing with PBS. The serially diluted OX40 antibodies were mixed with OX40L (R & D systems, Cat 1054-OX) at a final concentration of 664 ng/ml. The mixtures were added to the coated 96-well plate, and the isolated T cells were added to the wells and cultured for 3 days, and then the supernatant was collected. The concentration of IFNγ in the supernatant was detected by ELISA (R & D, Cat SIF50) according to the standard detection method recommended by the instructions.

In the functional experiment of Hu38E11 (IgG1 N297A) blocking the OX40L-OX40 interaction: the plate was coated with an anti-CD3 antibody, and OX40L, as native ligand of OX40, was added to stimulate T cells, and at the same time, free anti-OX40 antibody was added to the culture system, in order to detect the blocking effect of the antibody on the function induced by the binding of OX40L to OX40. Because the plate was not coated with the anti-OX40 antibody, the anti-OX40 antibody molecule was unable to stimulate T cells to secrete IFNγ in the absence of cross-linking. In addition, anti-OX40 antibody bound to the OX40 on the cell surface and blocked the binding of OX40L to OX40, thereby inhibiting the OX40L-induced secretion of IFNγ by T cells.

Figure 3:
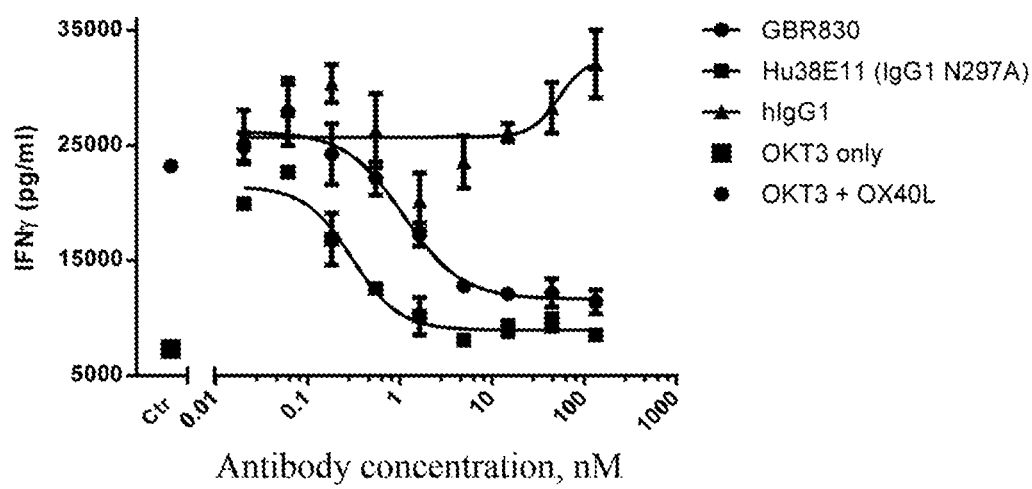
FIG. 3 shows the blocking effect of antibody Hu38E11 (IgG1 N297A) on the activation of T cells by OX40L, as detected by ELISA.

According to the results shown in FIG. 3, the antibody Hu38E11 (IgG1 N297A) can inhibit the secretion of IFNγ stimulated by OX40L at higher concentrations, indicating the blocking effect of the antibody on T cell activation by OX40L. Compared with GBR830, Hu38E11 (IgG1 N297A) had a stronger activity of blocking the OX40L-mediated T cell activation, and had a lower $IC_{50}$ value (0.3 nM for Hu38E11 (IgG1 N297A), and 1.1 nM for GBR830).

Example 9 Effects of Fc Regions of Humanized Antibodies on T-Cell Agonistic Activities The T-cell agonistic activity of Hu38E11 with a different Fc region can be evaluated by measuring the promoting effect of the antibody on NF-κB-mediated transcriptional activation in a luciferase reporter gene assay. Recombinant Jurkat cells (Jurkat-OX40-NF-κB-Luc; purchased from Chempartner) were constructed that overexpress human OX40 and have a luciferase reporter gene (Luc) under the control of NF-κB signaling. The anti-CD3 antibody (eBioscience, Cat 16-0037-85) was added to a 96-well plate at 100 ul/well, and the plate was coated overnight at 4° C. The unbound antibody was removed by washing with PBS. Then Jurkat-OX40-NF-κB-Luc cells and Raji cells were mixed at a ratio of 1:1 and then added to the coated 96-well plate, and then serially diluted Hu38E11 (IgG1), Hu38E11 (IgG1 N297A) or hIgG1 were added. After 5 hours of incubation, the relative amount of luciferase expression was detected with Steady-Glo (Promega) detection reagent.

Figure 4:
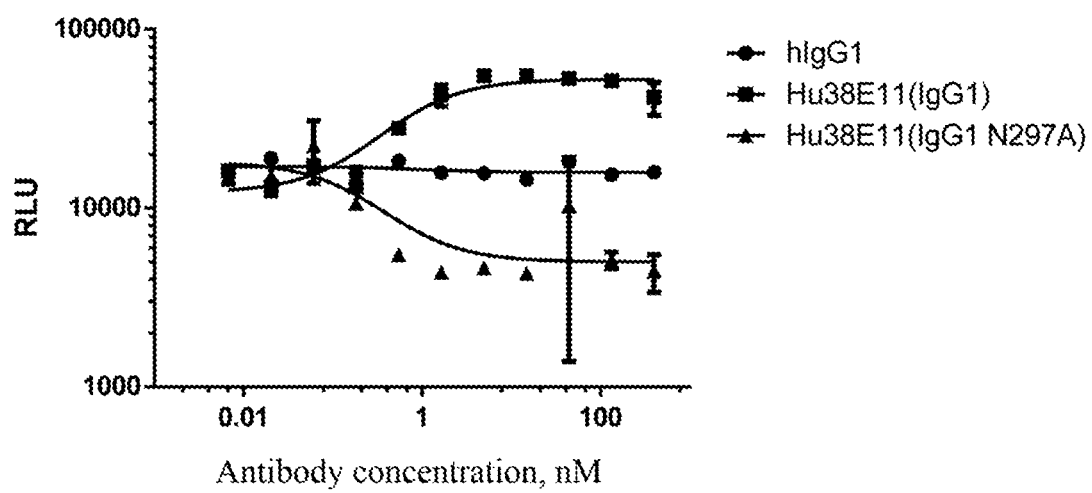
FIG. 4 shows the antagonistic activity of antibody Hu38E11 (IgG1 N297A) and the agonistic activity of antibody Hu38E11, as measured by luciferase reporter gene assay.

In this experiment, Hu38E11 (IgG1) initiated the downstream signaling of OX40 by cross-linking via FcγR receptors on the surface of Raji cells. This caused the expression of the reporter gene under the control of NF-κB ($EC_{50}$=0.70 nM). On the contrary, because of the N297A mutation, Hu38E11 (IgG1 N297A) cannot bind to FcγR receptors and cannot be cross-linked, and thus failed to activate the down-stream signaling of OX40. In addition, by blocking the binding of OX40 to OX40L expressed on the surface of Raji cells, the antibody showed a significant inhibitory effect on the expression of luciferase reporter gene under the control of NF-κB ($IC_{50}$=0.20 nM) (as shown in FIG. 4).

Example 10 Anti-Tumor Activity of Humanized Antibody Hu38E11 in B16F10 Subcutaneous Xenograft Tumor Model To study the anti-tumor activity of the antibody of the present invention, B16-F10 subcutaneous tumor model was established in C57BL/6-Tnfrsf4$^{em1Clin(hTBFRSF4)}$ transgenic mice expressing human OX40.

Mouse melanoma cells B16-F10 (ATCC® CRL-6475™) were cultured in RPMI1640 medium containing 10% fetal bovine serum. Tumor cells were suspended in RPMI1640 and implanted subcutaneously in the right flank of female transgenic mice (Jiangsu GemPharmatech Biotechnology Co., Ltd.) at a dose of 1×10$^5$ cells/mouse.

On the day of tumor cell inoculation (day 1), mice were randomly divided into 3 groups according to their body weights, 12 mice in the first group (h-IgG2), 13 mice in the second group (11D4 (IgG2)), and 13 mice in the third group (Hu38E11 (IgG2)). The antibodies were diluted with DPBS, and administered by a single intraperitoneal injection at a dose of 10 mg/kg. The tumor volumes (tumor volume=0.5× long diameter×short diameter$^2$), and body weights of the mice were measured regularly. The tumor inhibition rates of the antibody on day 15 and day 16 after administration were calculated.

The formula for calculating tumor inhibition rate is as follows: [(tumor volume in the control group−tumor volume in the treatment group)/tumor volume in the control group]× 100%. The formula for calculating the relative body weight of the mouse is: (weight of the mouse on the day of measurement/weight of the mouse at the time of grouping)× 100%.

Results: At a dose of 10 mg/kg, 11D4 (reference antibody) and Hu38E11 (IgG2, antibody of the present invention) showed the inhibition rates of tumor growth, 33.2% and 48.1%, respectively. In addition, during the course of the study, the weights of the mice in each group increased rapidly and no abnormal behavior was observed, indicating that the antibodies were well-tolerated by all the animals.

Example 11 Anti-Immune Rejection Activity of Humanized Antibody Hu38E11 (IgG1 N297A)

A graft-verus-host disease (GVHD) model was established by transplanting human primary peripheral blood mononuclear cells (hPBMC) from healthy volunteers to immunodeficient NOD-Prkdc$^{em26cd52}$Il2rg$^{em26cd22}$/Nju (NCG) mice, and was used to study the anti-immune rejection activity of the antibody of the present invention.

Primary human PBMC were isolated from whole blood obtained from healthy donors by density gradient centrifugation with Ficoll-Paque, and PBMCs were suspended in phosphate buffer (PBS).

On the day before PBMCs transplantation (day −1), mice were randomly divided into 7 groups according to their body weights. The groups were shown in Table 7. On the day of transplantation (day 0), all mice were irradiated with $^{137}$Cs γ ray at a single dose of 1.5 Gy TBI (total body irradiation), then antibody Hu38E11 (IgG1 N297A) and GBR830 diluted with PBS, were given i.v. weekly via tail at a dose of 1 mg/kg and at a volume of 5 mL/kg, and finally the mice received a single injection of PBMCs for 2.5×10$^7$ cells/mL at 0.2 mL/mouse at tail intravenous. The survival of the mice was monitored every day, and the body weight of the mice was measured regularly. The endpoint for euthanasia was when a relative body weight loss reached up to 20% and the survival time was recorded.

The formula for calculating the relative weight of the mouse is: (weight of the mouse on the day of measurement/weight of the mouse at the time of grouping)×100%.

TABLE 7

Grouping and dosage regimens of Hu38E11 (IgG1 N297A) treatment of hPBMC-induced graft-versus-host model

| Groups | Model treatment | Dose of administration (mg/kg) | Number of animals (Day 64/Day 0) | Dosage regimens |
|---|---|---|---|---|
| TBI group | 1.5 Gy irradiation | — | 6/6 | — |
| TBI + hIgG1 group | | 1 | 6/6 | Tail vein injection of 5 mL/kg IgG1, once a week |
| TBI + Hu38E11 (IgG1 N297A) group | | 1 | 6/6 | Tail vein injection of 5 mL/kg Hu38E11 (IgG1 N297A), once a week |
| hPBMC + hIgG1 group | 1.5 Gy irradiation, 5 × 10$^6$ cells/mouse hPBMC | 1 | 0/6 | Tail vein injection of 5 mL/kg hIgG1, once a week |
| hPBMC + GBR830 group | | 1 | 4/6 | Tail vein injection of 5 mL/kg GBR830, once a week |
| hPBMC + Hu38E11 (hIgG1 N297A) group | | 1 | 6/6 | Tail vein injection of 5 mL/kg Hu38E11 (IgG1 N297A), once a week |

Figure 5:
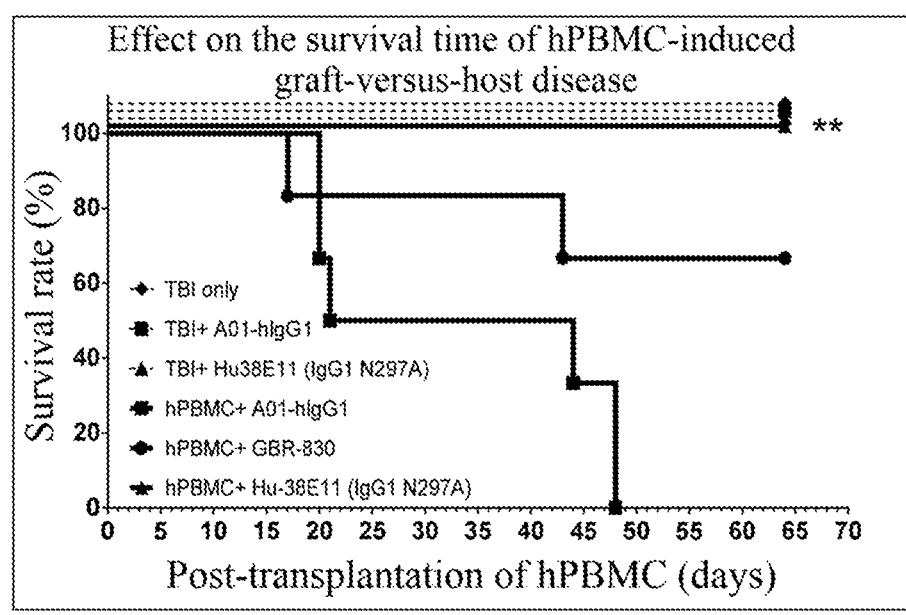
FIG. 5 shows the effect of antibody Hu38E11 (IgG1 N297A) on human PBMC-induced graft-versus-host disease.

The experimental results are shown in FIG. 5. In this experiment, all mice from the model control group (hPBMC+hIgG1 group) died on day 48, with a median survival time of 32.5 days; all mice treated with the antibody Hu38E11 (IgG1 N297A) of the present invention at 1 mg/kg survived until day 64 of the experiment, the median survival time cannot be calculated, and there was a significant difference compared with a model control group (hPBMC+hIgG1 group) (**: $p<0.01$). The survival rate of mice treated with positive reference antibody GBR830 at 1 mg/kg was 66.7% on day 64 of the experiment, the median survival time cannot be calculated, and there was no statistical difference compared with the model control group.

| Serial number (SEQ. ID NO.) | Sequence |
|---|---|
| 1 | QVQLQQPGAELVRPGSSVQLSCKASGYTFTSYWVDWVKQRPGQGLQWIGNIYPSDSETHYNQKFKDKATLTVDKSSSTAYMQLSSLTSEDSAVYYCARSYGYYGTWFAYWGQGTLVTVSA |
| 2 | QVQLVQSGAEVKKPGASVKVSCKASGYTFTSYWVDWVRQAPGQGLEWMGNIYPSDSETHYNQKFKDRVTMTRDTSTSTVYMELSSLRSEDTAVYYCARSYGYYGTWFAYWGQGTLVTVSS |
| 3 | QVQLVQSGAEVKKPGASVKVSCKASGYTFTSYWVDWVRQAPGQGLEWIGNIYPSDSETHYNQKFKDRVTMTVDTSTSTVYMELSSLRSEDTAVYYCARSYGYYGTWFAYWGQGTLVTVSS |
| 4 | QVQLVQSGAEVKKPGASVKVSCKASGYTFTSYWVDWVRQAPGQGLEWIGNIYPSDSETHYNQKFKDRVTMTVDTSTSTAYMELSSLRSEDSAVYYCARSYGYYGTWFAYWGQGTLVTVSS |
| 5 | QVQLVQSGAEVKKPGASVKLSCKASGYTFTSYWVDWVRQAPGQGLEWIGNIYPSDSETHYNQKFKDKVTLTVDTSTSTAYMELSSLRSEDSAVYYCARSYGYYGTWFAYWGQGTLVTVSS |
| 6 | DIVLTQSPASLAVSLGQRATISCRASESVDSSGNSFMHWYQQKPGQPPKLLIYRASNLESGIPARFSGSGSRTDFTLTINPVEADDVATYYCQQSNEDPWTFGGGTKLEIK |
| 7 | DIVMTQSPDSLAVSLGERATINCRASESVDSSGNSFMHWYQQKPGQPPKLLIYRASNLESGVPDRFSGSGSGTDFTLTISSLQAEDVAVYYCQQSNEDPWTFGGGTKLEIK |
| 8 | DIVMTQSPDSLAVSLGERATINCRASESVDSSGNSFMHWYQQKPGQPPKLLIYRASNLESGIPDRFSGSGSGTDFTLTISSLQAEDVAVYYCQQSNEDPWTFGGGTKLEIK |
| 9 | DIVMTQSPDSLAVSLGERATINCRASESVDSSGNSFMHWYQQKPGQPPKLLIYRASNLESGIPDRFSGSGSGTDFTLTISSVQAEDVAVYYCQQSNEDPWTFGGGTKLEIK |
| 10 | DIVLTQSPDSLAVSLGERATINCRASESVDSSGNSFMHWYQQKPGQPPKLLIYRASNLESGIPDRFSGSGSGTDFTLTISSVQAEDVAVYYCQQSNEDPWTFGGGTKLEIK |
| 11 | SYWVD |
| 12 | NIYPSDSETHYNQKFKD |
| 13 | SYGYYGTWFAY |
| 14 | RASESVDSSGNSFMH |
| 15 | RASNLES |
| 16 | QQSNEDPWT |
| 17 | CAGGTCCAACTGCAGCAGCCTGGGGCTGAGCTGGTGAGGCCTGGGTCTTCAGTGCAGTTGTCCTGCAAGGCTTCTGGCTACACCTTCACCAGCTACTGGGTGGATTGGGTGAAGCAGAGGCCTGGACAAGGCCTTCAATGGATTGGTAACATTTACCCTTCTGATAGTGAAACTCACTACAATCAAAAGTTCAAGGACAAGGCCACATTGACTGTAGACAAATCCTCCAGCACAGCCTACATGCAGCTCAGCAGCCTGACATCTGAAGACTCTGCGGTCTATTACTGTGCAAGATCTTATGGTTACTACGGGACCTGGTTTGCTTACTGGGGCCAAGGGACTCTGGTCACTGTCTCTGCA |

| Serial number (SEQ. ID NO.) | Sequence |
|---|---|
| 18 | CAGGTTCAGTTGGTTCAGTCTGGCGCCGAAGTGAAGAAACCTGGCGCCTC TGTGAAGGTGTCCTGCAAGGCTTCCGGCTACACCTTTACCAGCTACTGGG TCGACTGGGTCCGACAGGCTCCTGGACAAGGACTGGAATGGATGGGCAA CATCTACCCCTCCGACTCCGAGACACACTACAACCAGAAATTCAAGGAC CGCGTGACCATGACCAGAGACACCTCCACCAGCACCGTGTACATGGAAC TGTCCAGCCTGAGATCCGAGGACACCGCCGTGTACTACTGCGCCAGATCC TACGGCTACTACGGCACTTGGTTTGCCTATTGGGGCCAGGGCACACTGGT CACCGTTTCTTCC |
| 19 | GACATTGTGCTGACCCAATCTCCAGCTTCTTTGGCTGTGTCTCTAGGGCA GAGGGCCACCATATCCTGCAGAGCCAGTGAAAGTGTTGATAGTTCTGGC AATAGTTTTATGCACTGGTACCAGCAGAAACCAGGACAGCCACCCAAAC TCCTCATCTATCGTGCATCCAACCTAGAATCTGGGATCCCTGCCAGGTTC AGTGGCAGTGGGTCTAGGACAGACTTCACCCTCACCATTAATCCTGTGGA GGCTGATGATGTTGCAACCTATTACTGTCAGCAAAGTAATGAGGATCCGT GGACGTTCGGTGGAGGCACCAAACTGGAAATCAAA |
| 20 | GATATCGTGATGACCCAGTCTCCTGACAGCCTGGCTGTGTCTCTGGGCGA GAGAGCCACCATCAACTGCAGAGCCTCTGAGTCCGTGGACTCCTCCGGC AACTCTTTCATGCACTGGTATCAGCAGAAGCCCGGCCAGCCTCCTAAGCT GCTGATCTACAGAGCCTCCAACCTGGAATCTGGCGTGCCCGACAGATTCT CCGGCTCTGGCTCTGGCACAGATTTACCCTGACCATCAGCTCCCTGCAG GCCGAGGATGTGGCCGTGTACTACTGCCAGCAGTCCAACGAGGACCCCT GGACATTTGGCGGCGGAACAAAGCTGGAAATCAAG |
| 21 | ASTKGPSVFPLAPSSKSTSGGTAALGCLVKDYFPEPVTVSWNSGALTSGVHT FPAVLQSSGLYSLSSVVTVPSSSLGTQTYICNVNHKPSNTKVDKRVEPKSCD KTHTCPPCPAPELLGGPSVFLFPPKPKDTLMISRTPEVTCVVVDVSHEDPEVK FNWYVDGVEVHNAKTKPREEQYNSTYRVVSVLTVLHQDWLNGKEYKCKV SNKALPAPIEKTISKAKGQPREPQVYTLPPSREEMTKNQVSLTCLVKGFYPSD IAVEWESNGQPENNYKTTPPVLDSDGSFFLYSKLTVDKSRWQQGNVFSCSV MHEALHNHYTQKSLSLSPGK |
| 22 | ASTKGPSVFPLAPCSRSTSESTAALGCLVKDYFPEPVTVSWNSGALTSGVHTF PAVLQSSGLYSLSSVVTVPSSNFGTQTYTCNVDHKPSNTKVDKTVERKCCVE CPPCPAPPVAGPSVFLFPPKPKDTLMISRTPEVTCVVVDVSHEDPEVQFNWY VDGVEVHNAKTKPREEQFNSTFRVVSVLTVVHQDWLNGKEYKCKVSNKGL PAPIEKTISKTKGQPREPQVYTLPPSREEMTKNQVSLTCLVKGFYPSDIAVEW ESNGQPENNYKTTPPMLDSDGSFFLYSKLTVDKSRWQQGNVFSCSVMHEAL HNHYTQKSLSLSPGK |

The invention claimed is:

1. An isolated anti-OX40 antibody, comprising
   (1) heavy chain complementary determining regions (HCDRs), HCDR1, HCDR2 and HCDR3, wherein the HCDR1 comprises the amino acid sequence as set forth in SEQ ID NO: 11, the HCDR2 comprises the amino acid sequence as set forth in SEQ ID NO: 12, and the HCDR3 comprises the amino acid sequence as set forth in SEQ ID NO: 13;
   (2) light chain complementary determining regions (LCDRs), LCDR1, LCDR2 and LCDR3, wherein the LCDR1 comprises the amino acid sequence as set forth in SEQ ID NO: 14, the LCDR2 comprises the amino acid sequence as set forth in SEQ ID NO: 15, and the LCDR3 comprises the amino acid sequence as set forth in SEQ ID NO: 16; and
   (3) Fc region variant, which is human IgG1 N297A;
   wherein the amino acid residues in the Fc region are numbered in accordance with the EU numbering system.

2. The antibody of claim 1, comprising a heavy chain variable region (VH) and a light chain variable region (VL), wherein the VH comprises the amino acid sequence as set forth in SEQ ID NO: 2, and wherein the VL comprises the amino acid sequence as set forth in SEQ ID NO: 7.

3. The antibody of claim 1, which is a full-length antibody.

4. The antibody of claim 1, which has a binding affinity ($K_D$) to human OX40 of less than 10 nM, wherein the antibody comprises a heavy chain variable region (VH) and a light chain variable region (VL),
   wherein the VH comprises the amino acid sequence as set forth in SEQ ID NO: 2, and wherein the VL comprises the amino acid sequence as set forth in SEQ ID NO: 7 or 9; or
   wherein the VH comprises the amino acid sequence as set forth in SEQ ID NO: 4 and the VL comprises the amino acid sequence as set forth in SEQ ID NO: 7 or 8.

5. The antibody of claim 1, which is an OX40 antibody antagonist and has an activity for blocking OX40-mediated signal transduction, wherein the antibody comprises a heavy chain variable region (VH) and a light chain variable region (VL),
   wherein the VH comprises the amino acid sequence as set forth in SEQ ID NO: 2, and the VL comprises the amino acid sequence as set forth in SEQ ID NO: 7 or 9; or
   wherein the VH comprises the amino acid sequence as set forth in SEQ ID NO: 4 and the VL comprises the amino acid sequence as set forth in SEQ ID NO: 7 or 8; or
   wherein the VH comprises the amino acid sequence as set forth in SEQ ID NO: 3, and the VL comprises the amino acid sequence as set forth in SEQ ID NO: 9.

6. The antibody of claim 5, wherein the binding of the Fc region variant to FcγR is reduced or eliminated.

7. An immunoconjugate, comprising the antibody of claim 1 conjugated to one or more other substances.

8. An immune fusion, comprising the antibody of claim 1 fused to one or more other peptides or polypeptides by covalent linking.

9. A pharmaceutical composition, comprising the antibody of claim 1, or an immunoconjugate or immune fusion comprising the antibody, and a pharmaceutically acceptable carrier or excipient.

10. An isolated nucleic acid encoding the antibody of claim 1.

11. A recombinant vector or an expression vector, comprising one or more nucleic acids of claim 10, wherein the vector is suitable for recombinant production of the antibody.

12. An isolated host cell, comprising one or more recombinant vectors or expression vectors of claim 11.

13. A method for detecting OX40 in a sample, comprising:
   (a) contacting the sample with the antibody of claim 1, an immunoconjugate comprising the antibody of claim 1 conjugated to one or more other substances, or an immune fusion comprising the antibody of claim 1 fused to one or more other peptides or polypeptides by covalent linking; and
   b) detecting the formation of the complex of the antibody or the immunoconjugate or the immune fusion with the OX40 protein.

* * * * *